United States Patent
Springate et al.

(10) Patent No.: US 11,446,326 B2
(45) Date of Patent: Sep. 20, 2022

(54) HIGHLY SULFATED FUCANS FOR THE TREATMENT OF FIBROUS ADHESIONS

(71) Applicant: ARC Medical Devices Inc., Richmond (CA)

(72) Inventors: Christopher Michael Kevin Springate, Richmon (CA); Sailesh Haresh Daswani, Richmond (CA)

(73) Assignee: ARC Medical Devices, Richmond (CA)

( * ) Notice: Subject to any disclaimer, the term of this patent is extended or adjusted under 35 U.S.C. 154(b) by 0 days.

(21) Appl. No.: 17/260,275

(22) PCT Filed: Jul. 24, 2019

(86) PCT No.: PCT/CA2019/051030
§ 371 (c)(1),
(2) Date: Jan. 14, 2021

(87) PCT Pub. No.: WO2020/019081
PCT Pub. Date: Jan. 30, 2020

(65) Prior Publication Data
US 2021/0290658 A1    Sep. 23, 2021

Related U.S. Application Data

(60) Provisional application No. 62/711,335, filed on Jul. 27, 2018, provisional application No. 62/711,364, filed on Jul. 27, 2018, provisional application No. 62/711,372, filed on Jul. 27, 2018, provisional application No. 62/713,392, filed on Aug. 1, 2018, provisional application No. 62/713,399, filed on Aug. 1, 2018, provisional application No. 62/713,413, filed on Aug. 1, 2018, provisional application No. 62/722,135, filed on Aug. 23, 2018, provisional application No. 62/722,137, filed on Aug. 23, 2018, provisional application No. 62/755,311, filed on Nov. 2, 2018, provisional application No. 62/755,318, filed on Nov. 2, 2018, provisional application No. 62/755,328, filed on Nov. 2, 2018, provisional application No. 62/793,514, filed on Jan. 17, 2019, provisional application No. 62/793,654, filed on Jan. 17, 2019, provisional application No. 62/861,223, filed on Jun. 13, 2019, provisional application No. 62/861,228, filed on Jun. 13, 2019, provisional application No. 62/861,235, filed on Jun. 13, 2019.

(51) Int. Cl.
*A61K 31/737* (2006.01)
*A61P 41/00* (2006.01)
*C08B 37/00* (2006.01)

(52) U.S. Cl.
CPC ........... *A61K 31/737* (2013.01); *A61P 41/00* (2018.01); *C08B 37/0003* (2013.01); *C08B 37/0063* (2013.01)

(58) Field of Classification Search
None
See application file for complete search history.

(56) References Cited

U.S. PATENT DOCUMENTS

2008/0063682 A1* 3/2008 Cashman .............. A61K 36/03
514/54

OTHER PUBLICATIONS

Koyanagi, Biochemical Pharmacology 65 (2003) 173-179. (Year: 2003).*
Nishino, Carbohydrate Research, 229 (1992) 355-362. (Year: 1992).*
Lee, Algae, vol. 21(1): 157-160, 2006. (Year: 2006).*
Zhao, Mar. Drugs 2018, 16, 321. (Year: 2018).*

* cited by examiner

*Primary Examiner* — Layla D Berry
(74) *Attorney, Agent, or Firm* — King IP Law; Joshua King

(57) ABSTRACT

A highly-sulfated modified fucan comprising a therapeutically effective, medically acceptable fucan in a composition comprising a sulfate to fucose molar ratio of greater than or equal to about 1.2, 1.81 or 1.9 and/or a sulfate to fucose plus galactose molar ratio of greater than or equal to about 1.1, 1.2 or 1.3.

17 Claims, 3 Drawing Sheets

Base-treated
Sample B

Unmodified
Sample A

HIGHLY SULFATED FUCANS FOR THE TREATMENT OF FIBROUS ADHESIONS

CLAIM FOR PRIORITY

The present application claims the benefit of U.S. provisional patent application No. 62/711,364, filed Jul. 27, 2018; U.S. provisional patent application No. 62/711,372, filed Jul. 27, 2018; U.S. provisional patent application No. 62/711,335, filed Jul. 27, 2018; U.S. Provisional Patent Application Ser. No. 62/713,399, filed Aug. 1, 2018; U.S. provisional patent application No. 62/722,135, filed Aug. 23, 2018; U.S. provisional patent application No. 62/755,311, filed Nov. 2, 2018; U.S. provisional patent application No. 62/793,514, filed on Jan. 17, 2019; U.S. provisional patent application No. 62/861,223, filed Jun. 13, 2019; U.S. Provisional Patent Application Ser. No. 62/713,392, filed Aug. 1, 2018; U.S. provisional patent application No. 62/713,413, filed Aug. 1, 2018; U.S. provisional patent application No. 62/722,137, filed Aug. 23, 2018; U.S. provisional patent application No. 62/755,318, filed on Nov. 2, 2018; U.S. provisional patent application No. 62/861,228, filed Jun. 13, 2019; U.S. Provisional Patent Application Ser. No. 62/755,328, filed Nov. 2, 2018; U.S. provisional patent application No. 62/793,654, filed Jan. 17, 2019; and, U.S. provisional patent application No. 62/861,235, filed Jun. 13, 2019, all of which applications are incorporated herein by reference in their entirety.

BACKGROUND

Fucans (including fucoidan) are sulfated polysaccharides. In general terms, this means that they are molecules made up of a number of sugar groups, and also have sulfur atoms attached to the sugar groups. The main sugar group is called "fucose", which is sugar that has 6 carbon atoms and has the chemical formula $C_6H_{12}O_5$. "Fucoidan" (or fucoidin) indicates fucans derived from brown algae (seaweed). Fucans can exist alone, or in a mixture of other sugars, for example in a mixture of sugars such as xylose, galactose, glucose, glucuronic acid and/or mannose. These other sugars may be extracted from the seaweed or other source with the fucan. Although fucans are currently derived from natural sources such as the brown algae (seaweeds), sea cucumbers, etc., mentioned herein, "fucan" includes polymer molecules having the chemical and structural motifs of the fucans as discussed herein regardless of the ultimate source(s) of the fucans.

Fucoidan can be obtained from a variety of species of brown algae including but not limited to: *Adenocystis utricularis, Ascophyllum nodosum, Chorda filum, Cystoseirabies marina, Durvillaea antarctica, Ecklonia kurome, Ecklonia maxima, Eisenia bicyclis, Fucus evanescens, Fucus vesiculosis, Hizikia fusiforme, Himanthalia Elongata, Kjellmaniella crassifolia, Laminaria brasiliensis, Laminaria cichorioides, Laminaria hyperborea, Laminaria japonica, Laminaria saccharina, Lessonia trabeculata, Macrocystis pyrifera, Pelvetia fastigiata, Pelvetia Canaliculata, Saccharina japonica, Saccharina latissima, Sargassum stenophylum, Sargassum thunbergii, Sargassum confusum, Sargassum fusiforme* and *Undaria pinnatifida*. These exemplary species are all from the taxonomic class Phaeophyceae and the majority of these species fall into the families of Fucales and Laminariaceae.

Fucans including fucoidan have been shown to be efficacious in serving to inhibit, prevent, remove, reduce, or otherwise treat the formation of fibrous adhesions. They have also found use in the treatment of other related diseases and conditions.

Thus, there has gone unmet a need for fucan compositions having fucans with desired sulfation levels including in some embodiments such fucans being modified to have desired sulfation levels and/or medically viable, low endotoxin levels. Fucans are known to treat fibrous adhesions. Compositions comprising fucans with low sulfation levels have previously been demonstrated in the treatment of fibrous adhesions. The present compositions, systems and methods, etc., provide these and/or other advantages.

SUMMARY

Compositions, methods, systems, materials etc., are provided for modified fucans, for example high-sulfate fucans, that inhibit fibrous adhesions among other advantages. The compositions herein comprise highly sulfated fucans with high sulfate to fucose and high sulfate to total fucose plus galactose ratios.

The present compositions, methods, systems, etc., provide medically acceptable compositions comprising desired, modified highly sulfated fucans obtained from starting or initial fucan compositions (i.e., fucan compositions from which the modified fucans can be derived; such starting fucan compositions may or may not be crude or have been previously processed or purified, such as a feedstock fucan composition) as well as methods of obtaining such desired modified fucans and methods of use of such compositions.

In some aspects, the compositions, systems, methods, etc., herein are directed to medically acceptable compositions that comprise high-sulfate fucans.

In some aspects, the compositions, systems, methods, etc., herein can be directed to medically acceptable compositions that comprise a medically acceptable buffer or diluent and a therapeutically effective amount of a high-sulfate fucan having a sulfate to fucose molar ratio of greater than or equal to about 1.2 and/or a sulfate to fucose plus galactose molar ratio of greater than or equal to about 1.1. The sulfate to fucose molar ratio is greater than or equal to about 1.81 and/or the sulfate to fucose plus galactose molar ratio can be greater than or equal to about 1.2; the sulfate to fucose molar ratio can be greater than or equal to about 1.9 and/or the sulfate to fucose plus galactose molar ratio can be greater than or equal to about 1.3; the sulfate to fucose molar ratio can be between 1.81 and 2.85; and, the sulfate to fucose plus galactose molar ratio can be between 1.30 and 2.20.

The fucan can have a molecular weight distribution wherein at least 60% w/w of the distribution is greater than 100 kDa when measured using an aqueous gel permeation chromatography set up consisting essentially of:
one 300 mm analytical gel permeation chromatography column with a 7.8 mm inner diameter packed with hydroxylated polymethacrylate-based gel, having an effective molecular weight range of between about 50 kDa and about 5,000 kDa, one 300 mm analytical gel permeation chromatography column with a 7.8 mm inner diameter packed with hydroxylated polymethacrylate-based gel, having an effective molecular weight range of between about 1 kDa and about 6,000 kDa and one 40 mm guard column with a 6 mm inner diameter packed with hydroxylated polymethacrylate-based gel, the two analytical gel permeation chromatography columns and the one guard column contained in a column compartment at about 30° C.;
a refractive index detector at about 30° C.;
0.1M sodium nitrate mobile phase run at 0.6 mL/min; and
quantification against a peak molecular weight standard curve consisting essentially of a first dextran standard with a peak molecular weight of about 2,200 kDa, a second dextran standard with a peak molecular weight of between about 720 kDa and about 760 kDa, a third dextran standard with a peak molecular weight between about 470 kDa and about 510 kDa, a fourth dextran standard with a peak molecular weight between about 370 kDa and about 410 kDa, a fifth dextran standard with a peak molecular weight between about 180 kDa and about 220 kDa, and a sixth dextran standard with a peak molecular weight between about 40 kDa and 55 kDa.

The fucan can have a weight average molecular weight greater than 100 kDa; a molecular weight distribution wherein at least 90% w/w of the distribution can be greater than 100 kDa; a weight average molecular weight greater than 200 kDa, or a weight average molecular weight greater than 500 kDa. The fucan can have a molecular weight distribution wherein at least 90% w/w of the distribution can be greater than 500 kDa; a sulfation level of between 14% w/w and 60% w/w, 30% w/w and 55% w/w, 35% w/w and 52% w/w, 40% w/w and 60% w/w, 45% w/w and 60% w/w, 40% w/w and 55% w/w, or between 45% w/w and 55% w/w. The total carbohydrate content can be between 27% w/w and 80% w/w; the total fucose content as a percentage of the total carbohydrate content can be at least about 30% w/w; the total carbohydrate content can be at least about 50% w/w, and the total fucose content as a percentage of the total carbohydrate content can be at least about 70% w/w, 80% w/w, 90% w/w, or 95% w/w.

The fucan can have a total galactose content as a percentage of the total carbohydrate content below about 60% w/w, between about 2% w/w and 20% w/w, or below about 10% w/w. The total of glucuronic acid, mannose, rhamnose and xylose content as a percentage of the total carbohydrate content can be below about 30% w/w. The medically acceptable high-sulfate fucan composition can have a viscosity of between about 4 cP and 50 cP, 10 cP and 40 cP, or between about 15 cP and 30 cP. The medically acceptable high-sulfate fucan composition can be one of clear-colorless.

In some aspects, the compositions, systems, methods, etc., the methods herein comprise treating a fibrous adhesion in an animal comprising selecting a medically acceptable high-sulfate fucan composition herein to inhibit the fibrous adhesion and administering a therapeutically effective amount comprising a dosage range between 0.5 mg/kg and 50 mg/kg of the high-sulfate fucan to the site of a wound of the animal. Also provided herein are agents for treating a fibrous adhesion in an animal comprising a medically acceptable high-sulfate fucan composition herein for such treating. Also provided are agents for treating a fibrous adhesion in an animal comprising a selected medically acceptable high-sulfate fucan composition herein configured and composed to inhibit the fibrous adhesion and administering a therapeutically effective amount of it at a dosage range between 0.5 mg/kg and 50 mg/kg of the high-sulfate fucan to the site of a wound of the animal. Further provided herein is use of the medically acceptable high-sulfate fucan compositions herein for manufacture of a remedy for fibrous adhesions.

In further aspects, the compositions, systems, methods, etc., comprise treating a condition or disease in an animal comprising selecting a medically acceptable high-sulfate fucan composition herein to treat the condition or disease and administering a therapeutically effective amount between about 0.04 mg/kg and 25 mg/kg of the high-sulfate fucan in the composition to the animal. The therapeutically effective amount can be between about 0.2 mg/kg and 10 mg/kg, about 1 mg/kg and 5 mg/kg, about 1.5 mg/kg and 3 mg/kg, or about 5 mg/kg and 10 mg/kg. The condition or disease can be a fibrous adhesion at a target site in the animal, and the administering can comprise administering the therapeutically effective amount to the target site.

In further aspects, the compositions, systems, methods, etc., comprise medical compositions comprising between about 0.02 mg/mL and 100 mg/mL of the high-sulfate fucans herein, wherein the medical composition is configured and composed to treat a disease or condition in an animal.

The medical compositions can comprise between about 0.5 mg/mL and 5 mg/mL of the high-sulfate fucan, or about 2.5 mg/mL of the high-sulfate fucan.

The medical compositions herein can be a medical device, including a liquid medical device. The medical composition can be a pharmaceutical composition, including liquid pharmaceutical composition.

The methods herein include use of a dosage range comprising between about 0.01 mL/kg and 15 mL/kg, about 0.03 mL/kg and 4 mL/kg, about 0.06 mL/kg and 2 mL/kg or about 2 mL/kg and 4 mL/kg of the medical composition herein to treat a disease or condition in an animal.

The methods herein also include treating fibrous adhesions in a patient comprising administering the medical compositions herein to a target site in the patient. The treating of a selected disease or condition in a patient can comprise identifying a selected target site in a patient comprising or reasonably susceptible to having the selected disease or condition and then administering the medical compositions herein to the selected target site in the patient. The disease or condition can be fibrous adhesions, the selected target site can be a surgical site and the administering can be performed at least one of a) after opening a surgical wound at the surgical site, b) during surgery, and c) after closing the surgical wound. The administering can be performed after surgery but before closing the surgical wound. The administering takes less than 3 minutes, 2 minutes or 1 minute. The selected target site can be at least one of a lesion, abrasion and injury site. The selected target site can be at least one of a pelvic cavity, an abdominal cavity, a dorsal cavity, a cranial cavity, a spinal cavity, a ventral cavity, a thoracic cavity, a pleural cavity, a pericardial cavity, skin, a joint, a muscle, a tendon and a ligament.

In some aspects, also provided herein are methods for decreasing the sulfate level of a starting fucan or fucan composition to obtain a modified fucan. Such methods can comprise:
 adding to the starting fucan composition a base to produce a reaction mixture; and
 treating the reaction mixture with a quenching agent to render the base inactive, producing the modified fucan and desulfation remnant molecules, wherein the number average molecular weight, weight average molecular weight and peak average molecular weight of the modified fucan are within about 5% of the respective number average molecular weight, weight average molecular weight and peak average molecular weight of the starting fucan composition.

The starting fucan or fucan composition can be provided in a starting solution. The adding to the starting fucan composition the base further can comprise heating the solution. The base can comprise a hydroxide and/or oxide of an alkali metal, an alkaline earth metal and/or ammonium. The quenching agent can comprise at least one of an acid, a salt and water. The modified fucan comprises less sulfate than the starting fucan composition.

The methods can further comprise:
providing the starting fucan composition as a solid;
dissolving the starting fucan composition in a suitable non-aqueous solvent to produce a non-aqueous solution;
adding to the non-aqueous solution a sulfation agent to produce a reaction mixture; and
adding to the reaction mixture a quenching agent, producing a modified fucan and sulfation remnant molecules in a solution.

The methods further can comprise protonating the sulfate groups in the starting fucan composition to produce an acidified fucan composition before dissolving the starting fucan composition in a suitable non-aqueous solvent. The protonating can comprise dissolving the starting fucan composition in an aqueous solution, contacting the starting fucan composition with an acidic cation exchange resin and collecting the acidified fucan composition as a solid. The methods can also comprise collecting the acidified fucan composition as a solid can, which can comprise at least one of lyophilizing, spray drying and precipitating the solid acidified fucan composition from the aqueous solution. The sulfation agent can comprise at least one of $SO_3$-$Me_3N$, $SO_3$-$Et_3N$, $SO_3$-pyridine and $SO_3$-DMF. The non-aqueous solvent can comprise at least one of formamide, dimethylformamide, diethylformamide, dimethylsulfoxide, dichloromethane, chloroform, ethanol, methanol, n-butanol, 2-butanol, isopropanol and 1-propanol.

The adding to the non-aqueous solvent a sulfation agent to produce a reaction mixture further can comprise adding to the solvent a sulfation aid. The sulfation aid can be an acid scavenger, and the acid scavenger can be 2-methyl-2-butene. The adding to the non-aqueous solvent a sulfation agent further can also comprise incubating the reaction mixture for between about 5 minutes and about 50 hours, or about 1 hour and about 24 hours, and can be at a temperature between about 200 Celsius and about 60° Celsius. The quenching agent can comprise at least one of a salt and a buffer; the salt can be a bicarbonate salt. The adding to the reaction mixture a quenching agent further can comprise controlling the pH of the reaction mixture with at least one of an acid, a base and a buffer. The modified fucan can comprise more sulfate than the starting fucan composition.

The methods for increasing the sulfate level can also comprise:
providing a starting fucan composition as a solid;
suspending the starting fucan composition in a solvent, the solvent incapable of dissolving the fucan;
adding to the solvent containing the suspended starting fucan composition a sulfation agent, producing a reaction mixture comprising the modified fucan and the solvent;
separating the solid modified fucan from the solvent; and
quenching the solid modified fucan with a quenching agent.

The sulfation agent can be chlorosulfonic acid. The solvent can comprise at least one solvent with a relative polarity less than 0.765, such as at least one of dichloromethane, chloroform, methanol, ethanol, isopropanol, 1-propanol, n-butanol, 2-butanol, diethylether, hexane, heptane, benzene, decamethylcyclo-pentasiloxane, ethyl acetate, heptanol, octanol, decanol and dioxane. The values for relative polarity can be normalized from measurements of solvent shifts of absorption spectra. See for example Christian Reichardt, Solvents and Solvent Effects in Organic Chemistry, Wiley-VCH Publishers, 3rd ed., 2003. Adding a sulfation agent to produce a reaction mixture further can comprise incubating the reaction mixture for between about 5 minutes and about 50 hours, or between about 1 hour and about 24 hours. The reaction mixture can be incubated at a temperature between about 200 Celsius and about 600 Celsius. The quenching agent can comprise at least one of a salt and a buffer. Quenching the solid modified fucan further can comprise controlling the pH of the reaction mixture with at least one of an acid, a base and a buffer; and/or washing the solid modified fucan with an organic solvent comprising at least one solvent with a relative polarity less than 0.765. The modified fucan comprises more sulfate than the starting fucan composition.

These and other aspects, features and embodiments are set forth within this application, including the following Detailed Description and attached drawings. Unless expressly stated otherwise, all embodiments, aspects, features, etc., can be mixed and matched, combined and permuted in any desired manner.

Figure 1A:
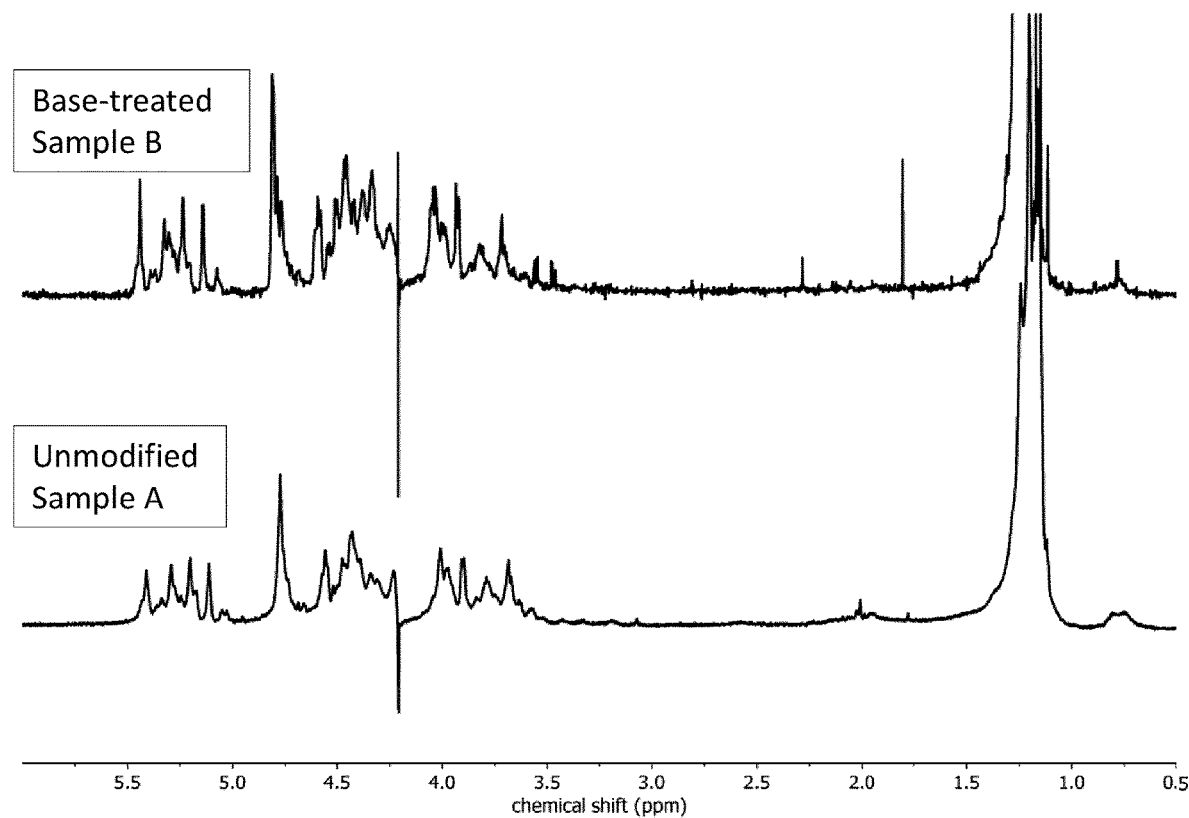
FIG. 1A depicts NMR results demonstrating that certain fucans treated according to methods herein undergo structural changes to the fucans.

The drawings present an exemplary embodiment of the present methods. Actual embodiments of the systems, methods, etc., herein may include further features or steps not shown in the drawings. The exemplifications set out herein illustrate embodiments of the systems, methods, etc., in one or more forms, and such exemplifications are not to be construed as limiting the scope of the disclosure in any manner. The embodiments herein are not exhaustive and do not limit the disclosure to the precise form disclosed, for example in the following detailed description.

DETAILED DESCRIPTION

The current compositions, systems, methods, etc., presented herein comprise modified fucans, for example high-sulfate fucans. The present compositions can be effective for medical treatments, post-surgical treatments, disease inhibition, etc. In some embodiments, the fucan is fucoidan. The present modified fucans can themselves be, or can be included on or in, medical devices, medical materials, combination products or in pharmaceutically acceptable, therapeutically and/or medically effective compositions.

Compositions

The current compositions, systems, etc., presented herein provide, in certain embodiments, fucans and medically acceptable high-sulfate fucans and high-sulfate fucans compositions comprising therapeutically effective amounts of high-sulfate fucans for the treatment of fibrous adhesions, such as surgical adhesions, arthritis, psoriasis or other diseases as desired.

The modified fucans presented herein may be used for a plurality of applications, including the treatment of fibrous adhesions and other targets such as other diseases and/or conditions. Treatment includes that the modified fucans reduce or prevent the development of a target disease or other condition, such as reducing or preventing the formation of fibrous adhesions at a target site, which is typically a selected target site identified by a surgeon or other practitioner as comprising or reasonably susceptible to having fibrous adhesions (or other diseases or conditions), and also includes elimination of existing diseases or other conditions, including for example the elimination of already-existing fibrous adhesions. For such treatment, the modified fucan is typically provided in a medically acceptable medical device, combination product, or pharmaceutically effective composition that contains additional components such as binders, adjuvants, excipients, etc., as well as, if desired, additional medically active substances such as secondary drugs that are contained within the composition but not attached to the modified fucan, and/or that can be attached to the modified fucan.

The current discussion discusses a relationship between the molar ratios of total sulfate to total fucose and the total sulfate to total fucose plus galactose of the modified fucans, and the prevention of post-surgical fibrous adhesions. The molar ratios of total sulfate to total fucose and the total sulfate to total fucose plus galactose of the modified fucans may hereafter be referred to as sulfation ratios. In some embodiments, the modified fucans can be high-sulfate fucans. The high-sulfate fucans herein can have at least one of a molar ratio of sulfate to fucose of greater or equal to 1.81 or about 1.9 and a molar ratio of sulfate to total fucose plus galactose of greater or equal to about 1.10 or about 1.3. The high-sulfate fucans can show greater efficacy in the treatment of fibrous adhesions than fucans with at least one of a molar ratio of sulfate to fucose of less than about 1.81 or about 1.9 and a molar ratio of sulfate to total fucose plus galactose less than about 1.10 or about 1.3.

In some embodiments, the fucans herein are modified to have a molar ratio of sulfate to fucose of 1.81, or about 1.85, 1.9, 2.0, 2.1, 2.3, 2.4, 2.5, 2.6, 2.7, 2.8, 2.9, 3.0, 3.1 3.2, 3.3, 3.4 or 3.5. The dispersity of the molar ratio of sulfate to fucose over the molecular weight distribution may increase with an increasing molecular weight, or decrease with an increasing molecular weight.

In some embodiments, the fucans herein are modified to have a molar ratio of sulfate to fucose between a lower and higher limit within a given molecular weight distribution, for example between about 1.81 to 1.9; 1.9 to 3.5; 1.8 to 3.0; 2.0 to 2.5; 1.9 to 2.3; or 2.0 to 3.0, or other combinations of the ratio levels herein. The dispersity of the molar ratio of sulfate to fucose over the molecular weight distribution may increase with an increasing molecular weight, or decrease with an increasing molecular weight.

The molecular weight distribution of the high-sulfate fucans may be measured using any desired, appropriate measurement system. Different systems can yield different readings or results from different compositions having essentially the same make-up, or even from the same batch when measured differently. One suitable measurement system is an aqueous gel permeation chromatography set up consisting essentially of one 300 mm analytical gel permeation chromatography column with a 7.8 mm inner diameter packed with hydroxylated polymethacrylate-based gel, having an effective molecular weight range of between about 50 kDa and about 5,000 kDa, one 300 mm analytical gel permeation chromatography column with a 7.8 mm inner diameter packed with hydroxylated polymethacrylate-based gel, having an effective molecular weight range of between about 1 kDa and about 6,000 kDa and one 40 mm guard column with a 6 mm inner diameter packed with hydroxylated polymethacrylate-based gel, the two analytical gel permeation chromatography columns and the one guard column contained in a column compartment at about 30° C., a refractive index detector at about 30° C., 0.1M sodium nitrate mobile phase run at 0.6 mL/min, and quantification against a peak molecular weight standard curve consisting essentially of a first dextran standard with a peak molecular weight of about 2,200 kDa, a second dextran standard with a peak molecular weight of between about 720 kDa and about 760 kDa, a third dextran standard with a peak molecular weight between about 470 kDa and about 510 kDa, a fourth dextran standard with a peak molecular weight between about 370 kDa and about 410 kDa, a fifth dextran standard with a peak molecular weight between about 180 kDa and about 220 kDa, and a sixth dextran standard with a peak molecular weight between about 40 kDa and 55 kDa. The peak molecular weight standard curve may further comprise a dextran standard with a peak molecular weight between 3 kDa and 5 kDa.

The high-sulfate fucans herein can have a molecular weight distribution wherein at least 50% w/w of the fucan has a molecular weight greater than 100 kDa. The high-sulfate fucans can have a molecular weight distribution wherein at least 40%, 50%, 60%, 70%, 80%, 90%, or 95% w/w of the fucan has a molecular weight greater than 100 kDa.

The high-sulfate fucans herein can have a molecular weight distribution wherein at least about 50%, 60%, 70%, 80%, or 90% w/w of the distribution is greater than 200 kDa. The high-sulfate fucans herein can have a molecular weight distribution wherein at least about 25%, 30%, 40%, 50%, 60%, 70%, or 75% w/w of the distribution is greater than 500 kDa. The high-sulfate fucans can have a molecular weight distribution wherein at least about 5%, 10%, 20%, 30%, or 40% w/w of the distribution is greater than 1600 kDa.

The high-sulfate fucans herein can have a weight average molecular weight greater than 100 kDa, for example between about 100 kDa and about 10,000 kDa, between about 200 kDa and about 8,000 kDa, between about 350 kDa and about 7,000 kDa, between about 450 kDa and about 6,000 kDa, between about 580 kDa and about 5,000 kDa, or between about 300 kDa and about 2,000 kDa.

In yet other embodiments, the high-sulfate fucans herein can have a peak molecular weight between about 70 kDa and 7,000 kDa, between about 100 kDa and 6,000 kDa, between about 200 kDa and 5,000 kDa, between about 250 kDa and 4,000 kDa, between about 350 kDa and 3,000 kDa, between about 500 kDa and 2,000 kDa, or between about 300 kDa and 1,000 kDa.

In yet other embodiments, the high-sulfate fucans herein can have a number average molecular weight between about 50 kDa and 3,000 kDa, between about 100 kDa and 2,000 kDa, between about 200 kDa and 1,500 kDa, or between about 300 kDa and 1,000 kDa, or between about 100 kDa and 600 kDa.

The high-sulfate fucans herein can have a sulfation level of between 10% w/w and 70% w/w, between about 20% w/w and 60% w/w, between about 30% w/w and 55% w/w, or between about 35% w/w and 52% w/w.

The high-sulfate fucans herein can have a total carbohydrate content of between about 27% w/w and 70% w/w, between about 30% w/w and 80% w/w, between about 40% w/w and 90% w/w, or between about 50% w/w and 96% w/w.

The high-sulfate fucans herein can have a fucose content as a percentage of total carbohydrate of about 30% w/w and 100% w/w, between about 40% w/w and 95% w/w, or between about 50% w/w and 90% w/w.

The high-sulfate fucans herein can have a galactose content as a percentage of total carbohydrate of about 0% w/w and 60% w/w, between about 2% w/w and 20% w/w, or between about 5% w/w and 10% w/w.

The high-sulfate fucans herein can have a glucuronic acid content as a percentage of total carbohydrate content between about 0% w/w and 10% w/w, a mannose content as a percentage of total carbohydrate content between about 0% w/w and 7% w/w, a rhamnose content as a percentage of total carbohydrate content between 0% w/w and 4% w/w, and a xylose content as a percentage of total carbohydrate content between 0% w/w and 20% w/w.

In some embodiments, the high-sulfate fucans herein, when dissolved at a concentration of 50 mg/mL in water, have a viscosity of between about 4 cP and about 50 cP, between about 5 cP and about 40 cP, between about 10 cP and about 30 cP, about 15 cP, about 20 cP and about 25 cP. In certain embodiments, the high-sulfate fucans herein, when dissolved in water at 1 mg/mL through 100 mg/mL form a solution that is one of clear and colorless, clear and light yellow or clear and light brown.

Methods

Methods, systems etc., are provided for modifying a starting fucan composition such as a feedstock fucan composition to increase or decrease the sulfation level of the fucan in the starting fucan composition. At least one of these methods may be used in the preparation of modified fucans comprising fucans with higher or lower sulfation ratios than the starting fucan composition, for example a molar ratio of sulfate to fucose of about 0.7, 1.0, 1.2, 1.5, 1.8, 1.9, 2.0, 2.1, 2.3, 2.5 or 2.8 and/or a molar ratio of sulfate to fucose plus galactose of about 0.7, 1.0, 1.2, 1.5, 1.8, 1.9, 2.0, 2.1, 2.3, 2.5 or 2.8. In some embodiments, the current disclosure presents modified fucans that are suitable for medical and surgical applications, for example, the prevention of fibrous adhesions.

The following paragraphs turn to a brief general discussion of some of the methodologies that can be used to create the modified fucans herein.

Extraction of Fucans from Fucan Sources

Methods for obtaining fucans from fucan sources are known. Fucans from some sources may be found to comprise higher sulfate levels compared to fucans from other sources, albeit lower sulfate levels than those discussed herein. Fucans may be obtained by the extraction of fucans from at least one of *Adenocystis utricularis*, *Ascophyllum nodosum*, *Chorda filum*, *Cystoseirabies marina*, *Durvillaea antarctica*, *Ecklonia kurome*, *Ecklonia maxima*, *Eisenia bicyclis*, *Fucus evanescens*, *Fucus vesiculosis*, *Hizikia fusiforme*, *Himanthalia Elongata*, *Kjellmaniella crassifolia*, *Laminaria brasiliensis*, *Laminaria cichorioides*, *Laminaria hyperborea*, *Laminaria japonica*, *Laminaria saccharina*, *Lessonia trabeculata*, *Macrocystis pyrifera*, *Pelvetia fastigiata*, *Pelvetia Canaliculata*, *Saccharina japonica*, *Saccharina latissima*, *Sargassum stenophylum*, *Sargassum thunbergii*, *Sargassum confusum*, *Sargassum fusiforme* and *Undaria pinnatifida*. These exemplary species are all from the taxonomic class Phaeophyceae and the majority of these species fall into the families of Fucales and Laminariaceae. In particular, highly sulfated fucans may be obtained by the extraction of fucans from *Ascophyllum nodosum*, *Ecklonia maxima*, *Eisenia bicyclis*, *Fucus vesiculosis*, *Laminaria hyperborea*, *Laminaria japonica*, *Laminaria saccharina*, *Macrocystis pyrifera*, *Pelvetia Canaliculata*, *Saccharina japonica*, *Saccharina latissima*, *Sargassum fusiforme* and *Undaria pinnatifida*.

Solvolytic Desulfation

An exemplary solvolytic desulfation method for the reduction in sulfate levels in polysaccharides including fucans can be found in, Vilela-Silva A. C et al, 2002, DOI: 10.1074/jbc.M108496200. The solvolysis of a fucan in dimethyl sulfoxide may be used to obtain fucans with various sulfation ratios. The solvolysis may be further controlled by varying the temperature and by addition of methanol during the desulfation reaction.

Tangential Flow Filtration

Some of the methods discussed herein utilize tangential flow filtration (TFF). Consistent with typical identification of tangential flow filtration (TFF) filters, the nominal molecular weight cut-off (MWCO) value for a given TFF filter will selectively retain on its retentate side a solution containing molecules that did not cross the filter barrier and thus generally have molecular weights and/or sizes greater than the molecular weight of molecules that do cross/permeate the barrier to the permeate side. Thus, molecular weight cut-off values for TFF filters are typically not absolute for any given polymer or nominal cut-off value: a given TFF filter will pass or retain some molecules both above and below the nominal molecular weight cut-off. The actual cut-off/selectively values and effects of a nominal TFF filter for a particular polymer can be routinely determined for the particular polymer.

A number of factors can affect the permeation behavior of the TFF filters. These factors may be dependent on the TFF filters themselves or dependent on an attribute of the target polymers, for example the folding behavior and folded structure of the target polymer can affect the behavior of the target polymer in crossing/not-crossing the TFF filter's MWCO barrier. Regarding the TFF filters themselves, as is known, a number of factors can affect the permeation behavior of the TFF filters. For example, manufacturing methods can cause a variety of hole sizes within the specific TFF filter, which variety can include holes both larger and smaller than the nominal MWCO. Thus, a TFF filter having a nominal molecular weight cut-off value will substantially pass/retain molecules at the nominal molecular weight cut-off value, but can also pass/retain some molecules below and/or above such value.

Gel Permeation Chromatography

Gel permeation chromatography was employed to evaluate the molecular weight distributions obtained for the experimental examples. There are a large number of different parameters, columns and standards available for use in gel permeation chromatography, resulting in a variety of instrumentation set-ups available for the analysis of molecular weight. For molecular weight determinations herein, the GPC were conducted using the following parameters: The mobile phase was 0.1M sodium nitrate run at 0.6 mL/min. The column compartment and detector were at 30° C. A Waters 2414 refractive index detector was used for detection.

Suitable GPC columns include GPC columns compatible with aqueous solvents, for example columns packed with at least one of sulfonated styrene-divinylbenzene, NH-functionalized acrylate copolymer network, modified silica and hydroxylated polymethacrylate-based gel. For the analyses herein, three columns were used in series, comprising one 40 mm long guard column with an inner diameter (ID) of 6 mm packed with 6 µm particle size hydroxylated polymethacrylate-based gel, followed by a first 300 mm analytical GPC column with a 7.8 mm ID packed with 12 µm particle size hydroxylated polymethacrylate-based gel that has an exclusion limit of about 7,000 kDa and an effective molecular weight range of between about 50 kDa and about 5,000 kDa, followed by a second 300 mm analytical GPC column with a 7.8 mm ID packed with 10 µm particle size hydroxylated polymethacrylate-based gel that has an exclusion limit of about 7,000 kDa and an effective molecular weight range of between about 1 kDa and about 6,000 kDa. The total effective molecular weight range of the column set up was between about 1 kDa and about 6,000 kDa. An example of this column set up can be Ultrahydrogel® guard-Ultrahydrogel® 2000-Ultrahydrogel® Linear columns connected in series.

Samples run were quantified against a standard curve comprising of traceable standards from the American Polymer Standards Corporation: DXT3755K (peak molecular weight=2164 kDa), DXT820K (peak molecular weight=745 kDa), DXT760K (peak molecular weight=621 kDa), DXT670K (peak molecular weight=401 kDa), DXT530K (peak molecular weight=490 kDa), DXT500K (peak molecular weight=390 kDa), DXT270K (peak molecular weight=196 kDa), DXT225K (peak molecular weight=213 kDa), DXT150K (peak molecular weight=124 kDa), DXT55K (peak molecular weight=50 kDa), DXT50K (peak molecular weight=44 kDa) and DXT5K (peak molecular weight=4 kDa), the peak molecular weights of these standards being between about 4 kDa and about 2,200 kDa. The standard curve used may, for example, include Dextran 3755 kDa, at least one of Dextran 50 kDa and Dextran 55 kDa, and between 3 to 6 additional traceable standards discussed herein, the calibration points being the peak molecular weights of the calibrants used. An example calibration curve may consist of DXT3755K, DXT 820K, DXT530K, DXT500K, DXT225K and DXT55K. The columns used herein had a total effective molecular weight range that encompassed and extended beyond the peak molecular weight range of the standards used for quantification of the fucans.

A molecular weight stated for a fucan/fucoidan polymer herein is a value of molecular weight about which there will always be a distribution of molecules of higher and lower molecular weights, increasing or decreasing in amount or percentage as the molecular weight increases or decreases away from the specified molecular weight. The distribution may, but is not required to, have a generally Gaussian or distorted Gaussian shape.

Results in the tables herein contain abbreviations used for certain characteristics of a molecular weight distribution. Gel permeation chromatography is denoted by GPC, peak retention time is denoted by PRT, peak molecular weight is denoted by PMW, weight average molecular weight is denoted by WAMW, number average molecular weight is denoted by NAMW, percentage distribution is denoted by % dist., molecular weight is denoted by MW, polydispersity index is denoted by PDI and molecular weight cutoff is denoted by MWCO.

Chemical Desulfation

The sulfation level of a starting fucan composition such as a feedstock fucan composition may be modified via chemical desulfation. For example, methods can comprise: providing a starting fucan composition; desulfating the fucan in the starting fucan composition with a base to produce the desired modified fucan; treating the desired modified fucan with a quenching agent to terminate the desulfation; and separating the desired modified fucan from desulfation remnant molecules. Desulfating the starting fucan composition may comprise heating the starting fucan composition.

Suitable bases include without limitation hydroxides and/or oxides of alkali metals, alkaline earth metals, zinc and/or ammonium, for example, sodium hydroxide, lithium hydroxide, potassium hydroxide, ammonium hydroxide, magnesium hydroxide, calcium hydroxide and zinc hydroxide. Suitable quenching agents include without limitation acids, salts and water, for example hydrochloric acid. Providing the starting fucan composition may comprise providing the starting fucan composition in a starting solution. Exemplary concentrations of the starting fucan composition in solution are between 0.01% w/v and 30% w/v. Exemplary concentrations of bases are between 0.01 M to 10 M.

Separating the desired modified fucan from desulfation remnant molecules may comprise diafiltering the desired modified fucan in solution over a suitable molecular weight cutoff (MWCO) TFF filter having a molecular weight cutoff greater than the largest desulfation remnant molecule, for example, a 5 kDa, 10 kDa, 30 kDa, 50 kDa, 70 kDa or 100 kDa molecular weight cut-off.

The methods may further comprise desalting the starting fucan composition before desulfating the fucan. The desalting may comprise diafiltrating the starting fucan composition in solution across a TFF filter, for example with distilled water. The TFF filter may have a molecular weight cutoff smaller than a desired molecular weight separation point or target in or for the desired modified fucan, for example, a 5 kDa, 30 kDa, 50 kDa, 70 kDa, 100 kDa, 200 kDa, 300 kDa, or 500 kDa molecular weight cut-off. The methods may further comprise pre-filtering the starting fucan composition through a suitable pre-filter to remove undesired particulate matter.

Chemical Sulfation

The sulfation level of a starting fucan composition such as a feedstock fucan composition may be modified via chemical sulfation. Exemplary methods can comprise: providing a starting fucan composition in an aqueous starting solution; protonating the sulfate groups on the fucan to obtain an acidified fucan composition; obtaining from the acidified fucan composition as a solid; re-solubilizing the solid acidified fucan composition in a suitable solvent, which can be a non-aqueous solvent, to provide a re-solubilized solution for the sulfation; adding to the re-solubilized solution containing the acidified fucan composition a sulfation agent; incubating the reaction mixture for a suitable amount of time at a desired reaction temperature; quenching the reaction mixture after the predetermined amount of time; and separating the modified fucan from the sulfation reaction remnant molecules.

The methods may further comprise desalting the starting fucan composition before sulfating the fucan. The desalting may comprise diafiltrating the starting fucan composition in solution across a TFF filter, for example with distilled water. The TFF filter can have a molecular weight cutoff smaller than a desired molecular weight separation point or target in or for the desired modified fucan for example, a 5 kDa, 30 kDa, 50 kDa, 70 kDa, 100 kDa, 200 kDa, 300 kDa, or 500 kDa molecular weight cut-off. The methods may further comprise pre-filtering the starting fucan composition through a suitable pre-filter to remove undesired particulate matter.

"Sulfation agent" is used according to its ordinary meaning and includes without limitation at least one of $SO_3$-$Me_3N$, $SO_3$-$Et_3N$, $SO_3$-pyridine and $SO_3$-DMF. A suitable amount of sulfation agent can be between 1:0.01 fucan: sulfation agent and 1:100 fucan:sulfation agent, for example 1:0.1 fucan:sulfation agent, 1:1 fucan:sulfation agent and 1:10 fucan:sulfation agent.

Protonating the sulfate groups on the fucan may comprise contacting the fucan with at least one of an acidified cation exchange resin and an acidified mixed charge resin. The contacting may comprise stirring a solution containing the starting fucan with the resin. The contacting may comprise recirculating a solution containing the starting fucan over the resin.

Obtaining a solid acidified fucan composition may involve without limitation, lyophilizing, spray drying and precipitating the solid acidified fucan composition from a solution. Re-solubilizing the solid acidified fucan may comprise solubilizing the solid acidified fucan composition in a solvent comprising of at least one of formamide, dimethylformamide, diethylformamide, dichloromethane, dimethylsulfoxide, chloroform, ethanol, methanol, n-butanol, 2-butanol, isopropanol and 1-propanol. Adding the sulfation agent may further comprising adding to the re-solubilized solution a sulfation aid. The sulfation aid may be an acid scavenger. The acid scavenger may be, for example, 2-methyl-2-butene.

Incubating the reaction mixture for a desired amount of time, which can be predetermined if desired, may comprise incubating the reaction mixture for between 5 minutes and 30 minutes, 1 hour, 4 hours, 10 hours, 24 hours and 50 hours. Suitable temperatures for incubating the reaction mixture can be between 200 Celsius and 40, 50 and 60° Celsius, for example at about 30, about 35 or about 40° Celsius. The incubation may involve without limitation stirring, shaking, rocking or otherwise agitating the reaction mixture.

Quenching the reaction mixture may comprise adding a quenching agent. Suitable quenching agents include without limitation salts and/or buffers, for example sodium bicarbonate, ammonium bicarbonate and potassium bicarbonate. Quenching the reaction mixture may further comprise controlling the pH of the reaction mixture with a suitable acid, base and/or buffer.

Separating the modified fucan from the sulfation reaction remnant molecules may involve filtration, for example, across a suitable molecular weight cut-off tangential flow filtration filter. Separating the modified fucan from the sulfation reaction remnant molecules may involve precipitation of the fucan, or the sulfation reaction remnant molecules, from the reaction mixture.

Another exemplary embodiment of chemical sulfation comprises: providing a solid starting fucan composition suspended in a suitable solvent for the sulfation, the solvent incapable of dissolving the fucan; adding a sulfation agent; incubating the reaction mixture for a predetermined amount of time at a predetermined reaction temperature; separating the solid modified fucan from the solvent; washing the solid modified fucan to remove any solvent remnants; quenching the solid modified fucan; and separating the modified fucan from the sulfation reaction remnant molecules.

Suitable sulfation agents include, for example, chlorosulfonic acid. Suitable solvents include organic solvents with a relative polarity less than 0.765, for example, dichloromethane, chloroform, methanol, ethanol, isopropanol, 1-propanol, n-butanol, 2-butanol, diethylether, hexane, heptane, benzene, decamethylcyclo-pentasiloxane, ethyl acetate, heptanol, octanol, decanol and dioxane.

Incubating the reaction mixture for a predetermined amount of time may comprise incubating the reaction mixture for between 5 minutes and 30 minutes, 1 hour, 4 hours, 10 hours, 24 hours and 50 hours. Incubating the reaction mixture for a temperature may comprise incubating the reaction mixture at between 20° C. and 40° C., 50° C. and 60° C., for example at about 30° C., about 35° C. or about 40° C. The incubation may involve without limitation stirring, shaking, rocking or otherwise agitating the reaction mixture.

Separating the solid modified fucan from the solvent may comprise one of more of, for example, centrifugation, filtration, sedimentation and hydrodynamic fluid separation. Washing the solid modified fucan may involve washing with a solvent or solvent mixture composed of at least one organic solvent with a relative polarity less than 0.765, for example, dichloromethane, chloroform, methanol, ethanol, isopropanol, 1-propanol, n-butanol, 2-butanol, diethylether, hexane, heptane, benzene, decamethylcyclo-pentasiloxane, ethyl acetate, heptanol, octanol, decanol and dioxane.

Quenching the reaction mixture may comprise solubilizing the solid modified fucan in an aqueous solvent with a suitable quenching agent. Suitable quenching agents include without limitation salts and/or buffers, for example sodium bicarbonate, ammonium bicarbonate and potassium bicarbonate. Quenching the reaction mixture may further comprise controlling the pH of the solubilized modified fucan with a suitable acid, base and/or buffer.

Separating the modified fucan from the sulfation reaction remnant molecules may involve filtration, for example, across a suitable molecular weight cut-off tangential flow filtration filter. Separating the modified fucan from the sulfation reaction remnant molecules may involve precipitation of the fucan, or the sulfation reaction remnant molecules, from the reaction mixture.

Chemical Structural Modification

The methods, systems etc. discussed herein can comprise chemical structural modification of the fucan composition, particularly the fucans in the fucan composition. The chemical structural modification may involve removal of functional groups from the fucan, for example, O-acetyl, N-acetyl, methoxy, hydroxyl, carboxylic and/or sulfate functional groups from the fucan structure. The chemical structural modification may involve the use of a wide variety of chemical reagents, for example, acids, bases, detergents and/or oxidizing agents.

Diseases and Conditions

Fibrous Adhesions

A fibrous adhesion is a type of scar that forms between two parts of the body, usually after surgery (surgical adhesion). Fibrous adhesions can cause severe problems. For example, fibrous adhesions involving the female reproductive organs (ovaries, Fallopian tubes) can cause infertility, dyspareunia and severe pelvic pain. Fibrous adhesions that occur in the bowel can cause bowel obstruction or blockage, and fibrous adhesions can also form in other places such as around the heart, spine and in the hand. In addition to surgery, fibrous adhesions can be caused for example by endometriosis, infection, chemotherapy, radiation, trauma and cancer.

A variety of fibrous adhesions are discussed in this document. Terms such as surgical adhesions, post-surgical adhesions, postoperative adhesions, adhesions due to pelvic inflammatory disease, adhesions due to mechanical injury, adhesions due to radiation, adhesions due to radiation treatment, adhesions due to trauma, and adhesions due to presence of foreign material all refer to adherence of tissues to each other due to a similar mechanism and are all included in the term fibrous adhesions.

Fibrous adhesion formation is a complex process in which tissues that are normally separated in the body grow into each other. Surgical adhesions (also known as post-surgical adhesions) develop from the otherwise normal wound healing response of the tissues to trauma and have been reported to occur in over two-thirds of all abdominal surgical patients (Ellis, H., *Surg. Gynecol. Obstet.* 133: 497 (1971)). The consequences of these fibrous adhesions are varied and depend upon the surgical site or other site, such as a disease site, involved. Problems may include chronic pain, obstruction of the intestines and even an increased risk of death after cardiac surgery (diZerega, G. S., *Prog. Clin. Biol. Res.* 381: 1-18 (1993); diZerega, G. S., *Fertil. Steril.* 61:219-235 (1994); Dobell, A. R., Jain, A. K., *Ann. Thorac. Surg.* 37: 273-278 (1984)). In women of reproductive age, fibrous adhesions involving the uterus, fallopian tubes or ovaries are estimated to account for approximately 20% of all infertility cases (Holtz, G., *Fertil. Steril.* 41: 497-507 (1984); Weibel, M. A. and Majno, G. *Am. J. Surg.* 126: 345-353 (1973)).

The process of fibrous adhesion formation initially involves the establishment of a fibrin framework and normal tissue repair. The normal repair process allows for fibrinolysis alongside mesothelial repair. However, in fibrous adhesion formation the fibrin matrix matures as fibroblasts proliferate into the network and angiogenesis occurs resulting in the establishment of an organized fibrous adhesion within about 3 to 5 days (Buckman, R. F., et al., *J. Surg. Res.* 21: 67-76 (1976); Raferty, A. T., *J. Anat.* 129: 659-664 (1979)). Inflammatory processes include neutrophil activation in the traumatized tissues, fibrin deposition and bonding of adjacent tissues, macrophage invasion, fibroblast proliferation into the area, collagen deposition, angiogenesis and the establishment of permanent fibrous adhesion tissues.

Various attempts have been made to prevent surgical adhesions. These involve pharmacological approaches targeted at influencing the biochemical and cellular events that accompany surgical traumas well as barrier methods for the separation of affected tissues. For example, the use of peritoneal lavage, heparinized solutions, procoagulants, modification of surgical techniques such as the use of microscopic or laparoscopic surgical techniques, the elimination of talc from surgical gloves, the use of smaller sutures and the use of physical barriers (films, gels or solutions) aiming to minimize apposition of serosal surfaces, have all been attempted. Currently, preventive therapies also include prevention of fibrin deposition, reduction of inflammation (steroidal and non-steroidal anti-inflammatory drugs) and removal of fibrin deposits.

Interventional attempts to prevent the formation of post-surgical adhesions have included the use of hydroflotation techniques or barrier devices. Hydroflotation involves the instillation of large volumes of polymer solutions such as dextran (Adhesion Study Group, *Fertil. Steril.* 40:612-619 (1983)), or carboxymethyl cellulose (Elkins, T. E., et al., *Fertil. Steril.* 41:926-928 (1984)), into the surgical space in an attempt to keep the organs apart. Synthetic barrier membranes made from oxidized regenerated cellulose (e.g., Interceed™), polytetrafluoroethylene (Gore-tex surgical membrane) and fully resorbable membranes made from a modified hyaluronic acid/carboxymethylcellulose (HA/CMC) combination (Seprafilm™) have also been used to reduce post-surgical adhesion formation in both animals and humans (Burns, J. W., et al., *Eur. J. Surg. Suppl.* 577: 40-48 (1997); Burns, J. W., et al., *Fertil. Steril.* 66:814-821 (1996); Becker, J. M., et al., *J. Am. Coll. Surg.* 183:297-306 (1996)).

The success of these HA/CMC membranes may derive from their ability to provide tissue separation during the peritoneal wound repair process when fibrous adhesions form. The membranes were observed to form a clear viscous coating on the injured tissue for 3-5 days after application, a time period that is compatible with the time course of post-surgical adhesion formation (Ellis, H., *Br. J. Surg.* 50: 10-16 (1963)). Unfortunately, limited success has been seen with these methods.

Peritonitis involves inflammation of the peritoneum. Peritonitis can cause severe problems. For example, abdominal pain, abdominal tenderness and abdominal guarding. Peritonitis may involve spontaneous, anatomic and/or peritoneal dialysis related inflammation. Peritonitis may involve an infection, for example, perforation of a hollow viscus, disruption of the peritoneum, spontaneous bacterial peritonitis, and systemic infections may result in infection and peritonitis. Peritonitis may also not involve an infection, for example, leakage of sterile body fluids into the peritoneum, and sterile abdominal surgery may result in peritonitis. Various attempts have been made to prevent and/or treat peritonitis. For example, general supportive measures such as intravenous rehydration, antibiotics, and surgery. There is an unmet need for compounds, compositions, methods and the like (including delivery approaches) to inhibit, or otherwise treat and/or prevent, peritonitis, preferably more effectively with few side effects.

The high-sulfate fucans discussed herein can be used to treat fibrous adhesions in a patient and can be included as a component of, or be, a high-sulfate fucan medical device, combination or pharmaceutical product configured and composed to treat fibrous adhesions. For example, a high-sulfate fucan medical device comprising between about 0.02 mg/mL to about 100 mg/mL, for example 0.1 mg/mL, 0.2 mg/mL, 0.3 mg/mL, 0.5 mg/mL, 0.9 mg/mL, 1 mg/mL, 2.5 mg/mL, 5 mg/mL 7.5 mg/mL, of a high-sulfate fucan herein dissolved in a physiological salt solution. The physiological salt solution can be, for example, Lactated Ringer's Injection USP (LRS), normal saline and physiological Dextran solution.

The high-sulfate fucan medical devices, which can be liquid medical devices, herein can contain pharmaceutically acceptable excipients such as buffers, stabilizers, preservatives, adjuvants, etc. Such high-sulfate fucan medical devices can be used to treat fibrous adhesions pre-during, or post-surgery by administering between about 0.01 mL/kg (per kilogram bodyweight of the patient or target) to about 10 mL/kg or 15 mL/kg of the fucan medical devices in the preceding paragraph. Doses include, for example, about 0.03 mL/kg, 0.1 mL/kg, 0.2 mL/kg, 0.4 mL/kg, 0.5 mL/kg, 0.6 mL/kg, 1 mL/kg, 1.2 mL/kg, 2 mL/kg, 3 mL/kg, 4 mL/kg, 5 mL/kg, 8 mL/kg, 10 mL/kg and 15 mL/kg of the high-sulfate fucan medical device to the surgical site of the patient. In further embodiments, such high-sulfate fucan medical devices can be used to treat fibrous adhesions at any selected target site, for example lesions, abrasions, injury sites, surgical sites and post-surgical sites by administering between about 0.04 mg/kg or 0.1 mg/kg to about 25 mg/kg or 50 mg/kg. Some examples of such doses include, for example, about 0.04 mg/kg, 0.075 mg/kg, 0.1 mg/kg, 0.2 mg/kg, 0.5 mg/kg, 1 mg/kg, 1.3 mg/kg, 2 mg/kg, 3 mg/kg, 4 mg/kg, 5 mg/kg, 7.5 mg/kg, 8 mg/kg, 10 mg/kg, 15 mg/kg, 20 mg/kg, 25 mg/kg and 50 mg/kg of the fucans herein, including for example the high-sulfate fucans herein, to the surgical site of the patient.

The administering can be accomplished, for example, by instilling a liquid medical device generally throughout the target area; directing the liquid medical device at a specific location(s) within the target area; spraying the liquid medical device generally or at a specific location(s) within the target area; or, spraying or otherwise delivering the liquid medical device via an applicator, which can be a spray applicator through a trocar, catheter, endoscope or other minimally invasive device, onto a specific location(s) that a surgeon or other practitioner has identified as particularly susceptible to or concerning for development of fibrous adhesions. In another aspect, the administering can be done after opening of the surgical wound but before the surgical procedure; during the surgical procedure, or after the surgical procedure but before the surgical wound has been closed. If desired, the liquid medical device can also be administered after the surgery is completed (for example through a syringe and needle) and can be administered to non-surgical target sites as well. The surgical site of the patient can be, for example, at least one of the pelvic cavity, abdominal cavity, dorsal cavity, cranial cavity, spinal cavity, ventral cavity, thoracic cavity, pleural cavity, pericardial cavity, skin, joints or muscles. The administering of the high-sulfate fucan medical device into the surgical site of the patient can be accomplished in less than about 15 minutes, 10 minutes, 8 minutes, 6 minutes, 5 minutes, 4 minutes, 3 minutes, 2 minutes, 1 minute, 45 seconds, 30 seconds, 20 seconds, 15 seconds, 10 seconds and 5 seconds.

Examples of administering the high-sulfate fucan medical device to a surgical site include without limitation administering the high-sulfate fucan medical device at the surgical site of a Cesarean section surgical procedure; a microvascular free flap reconstruction surgical procedure, a full thickness skin graft surgical procedure, a V-Y advancement flap surgical procedure, a fasciocutaneous rotation flap surgical procedure, an arthroplasty surgical procedure, a mastectomy surgical procedure, a sequestrectomy surgical procedure, a saucerization surgical procedure, an osteotomy surgical procedure, an osteoplasty surgical procedure, a patellectomy surgical procedure, a synovectomy surgical procedure, a capsulectomy surgical procedure, a tendon or ligament repair surgical procedure, a tenolysis surgical procedure, a tenotomy surgical, a fasciotomy surgical procedure, a meniscal repair surgical procedure, a vertebrectomy surgical procedure, a ethmoidectomy surgical procedure, a Caldwell Luc's operation surgical procedure, a dacryocystorhinostomy surgical procedure, a lysis nasal synechia surgical procedure, a thymectomy surgical procedure, a pneumonolysis surgical procedure, a pneumonectomy surgical procedure, thoracoplasty surgical procedure, a bilobectomy surgical procedure, a portal hypertension surgery surgical procedure, a splenectomy surgical procedure, a esophagectomy surgical procedure, a peritonitis surgery surgical procedure, a gastrectomy surgery surgical procedure, a jejunojejunostomy surgery surgical procedure, a laparoscopic cholecystectomy surgery surgical procedure, a laparoscopic common bile duct exploration surgical procedure, a gastroenterostomy surgical procedure, a bariatric surgery surgical procedure, a bowel resection & anastomosis surgical procedure, a segemental hepatectomy surgical procedure, a lobectomy surgical procedure, a pancreatomy surgical procedure, a pancreaticoduodenectomy surgical procedure, a tumor resection surgical procedure, a laparoscopic nephrectomy surgical procedure, a cystectomy surgical procedure, an abdominal or pelvic adhesion lysis surgical procedure, a hysterosalpingostomy surgical procedure, a salpingoplasty surgical procedure, an ectopic pregnancy laparoscopic surgery surgical procedure, a joint replacement surgery surgical procedure, a broken bone repair surgical procedure, a hysterectomy surgical procedure, a gallbladder removal surgical procedure, a heart bypass surgical procedure, an angioplasty surgical procedure, an atherectomy surgical procedure, a breast biopsy surgical procedure, a carotid endarterectomy surgical procedure, a cataract surgery surgical procedure, a coronary artery bypass surgical procedure, a dilation and curettage surgical procedure, a hernia repair surgical procedure, a lower back pain surgery surgical procedure, a partial colectomy surgical procedure, prostatectomy surgical procedure and a tonsillectomy surgical procedure, after opening the surgical wound, during surgery, before closing the surgical wound and/or after closing the surgical wound.

Cancers Generally

Cancer has been the second leading cause of death in the U.S. and accounts for over 20% of all mortalities. Cancer is a proliferative disease and is characterized by the uncontrolled division of certain cells, which may lead to the formation of one or more tumors. A number of methods are used to treat cancer, including surgery, radiation, chemotherapy and combinations thereof. Although surgery is a relatively common method used for some localized tumors, there is still a significant chance of tumor recurrence after tumor excision.

Treating cancers and other proliferative diseases has been limited by the potential for damage or toxicity to non-cancerous, healthy tissues. In radiation and surgical treatments, the procedure has been generally confined to and proximal to the tumor sites. However, there can be significant risk to patients undergoing surgical removal of cancerous tissues (e.g., in removal of prostate or brain tumors there can be a significant risk of non-repairable damage to surrounding vital tissues, for example via potential reduced need for resection of non-tumor tissues. Furthermore, in focused radiation treatment, which has been given as a first line treatment for prostate cancer, there are similar risks. In the chemotherapeutic treatment of cancer, the drug has been administered systemically, so that the whole body is exposed to the drug. These drugs are designed to be toxic to cancer cells, but they are also (generally) toxic to non-cancerous cells so that patients become quite ill when undergoing drug treatments for cancer. Through experience, oncologists are able to give doses of these drugs that may be tolerated by some patients. However, these doses are often not successful in treating cancers.

One problem with any method of treating cancer has been the local recurrence of the disease. For example, approximately 700,000 Americans are diagnosed with localized cancer annually (approximately 64% of all cancer patients) and almost half a million are treated using surgical methods. Unfortunately, 32% of patients treated with surgery relapse after the initial treatment (approximately 21% relapse at the initial surgical site and 11% at distant metastatic sites). Almost 100,000 patients die annually due to localized recurrence of cancer. This has been especially true in breast cancer where 39% of patients undergoing lumpectomy will experience local recurrence of the disease.

Staging is a method of judging the progress of the cancer (solid tumor) in a patient. A simplified approach puts patients into three groups or stages based on how far the cancer has advanced:

Stage 1: The cancer can be treated by surgically removing part of the organ. This is also known as the resectable stage.

Stage 2: The cancer has advanced past the point of being resectable but is still confined to the organ itself.

Stage 3: The tumor has spread to other organs.

Many cancers are treated with anti-proliferative agents including, for example, 5-fluorouracil (Efudex®), vinca alkaloids (for example, vincristine (Oncovin®)), anthracyclines (for example, doxorubicin (Adriamycin®)), cisplatin (Platinol-AQ®), gemcitabine hydrochloride (Gemzar®), methotrexate and paclitaxel. Some examples of the toxicities associated with the anti-proliferative agents, methotrexate and paclitaxel, are discussed elsewhere herein. Methotrexate has been used to treat several cancers including, for example, bladder, breast, cervical, head and neck, hepatic, lung, and testicular cancers. Paclitaxel has been used to treat several cancers including, for example, ovarian, breast, and non-small cell lung cancers (*Compendium of Pharmaceutical and Specialties Thirty-fifth Edition,* 2000).

Toxicities due to 5-fluorouracil can include cardiovascular toxicity such as myocardial ischemia; central nervous system toxicities such as euphoria, acute cerebellar syndrome and ataxia; dermatologic toxicities such as alopecia and dermatitis; gastrointestinal toxicities such as nausea, vomiting and oral or gastrointestinal ulceration; hematologic toxicities such as leukopenia, thrombocytopenia and anemia; hypersensitivity toxicities such as anaphylaxis and contact hypersensitivity; ocular toxicities such as increased lacrimation, photophobia and conjunctivitis; and, other toxicities such as fever. 5-fluorouracil has been used to treat many cancers including, for example, breast, colorectal, gastric, hepatic, bladder, head and neck, non-small cell lung, ovarian, pancreatic, and prostate cancers (*Compendium of Pharmaceutical and Specialties Thirty-fifth Edition,* 2000).

Toxicities due to vincristine include central nervous system toxicities such as seizures in children and hallucinations; dermatologic toxicity such as alopecia; extravasation toxicity such as vesicant; gastrointestinal toxicities such as nausea, vomiting, constipation and stomatitis; hematologic toxicity such as myelosuppression; neurologic toxicities such as peripheral neuropathy and autonomic neuropathy; ocular toxicities such as double vision, transient blindness and optic atrophy; renal/metabolic toxicities such as urinary retention, hyperuricemia and bladder atony; respiratory toxicity such as shortness of breath; and, other toxicity such as fever in children. This anti-proliferative agent has been used to treat several cancers including, for example, Hodgkin's disease, small cell lung, Wilm's tumor, and testicular cancers (*Compendium of Pharmaceutical and Specialties Thirty-fifth Edition,* 2000).

Toxicities due to doxorubicin include cardiovascular toxicities such as electrocardiographic abnormalities and cardiomyopathy; dermatologic toxicities such as alopecia and nail changes; extravasation hazard toxicity such as vesicant; gastrointestinal toxicities such and nausea, vomiting and stomatitis; genitourinary toxicity such as red coloration of urine; hematologic toxicity such as myelosuppression; hypersensitivity toxicities such as anaphylaxis and skin rash; ocular toxicity such as conjunctivitis; reproductive toxicity such as infertility; and, other toxicity such as hyperuricemia. This anti-proliferative agent has been used to treat several cancers including, for example, breast, small cell lung, and ovarian cancers (*Compendium of Pharmaceutical and Specialties Thirty-fifth Edition,* 2000).

Toxicities due to cisplatin include cardiovascular toxicity such as electrocardiographic changes; dermatologic toxicity such as hyperpigmentation; extravasation hazard toxicity such as irritant; gastrointestinal toxicities such as nausea and vomiting; hematologic toxicities such as myelosuppression and hemolytic anemia; hypersensitivity toxicity such as anaphylactic; neuromuscular toxicity such as peripheral neuropathy and acute encephalopathy; ocular toxicity such as retrobulbar neuritis; otologic toxicities such as hearing loss and tinnitus; renal/metabolic toxicities such as toxic nephropathy and hypokalemia; and, other toxicity such as infertility. This anti-proliferative agent has been used to treat several cancers including, for example, bladder, small cell lung, ovarian, testicular, brain, breast, cervical, head and neck, hepatoblastoma, and thyroid cancers (*Compendium of Pharmaceutical and Specialties Thirty-fifth Edition,* 2000). Toxicities due to gemcitabine hydrochloride include, for example, hematologic toxicities such as myelosuppression; gastrointestinal toxicities such as nausea, vomiting and stomatitis; hepatic toxicities such as transient elevations of serum transaminases; renal toxicities such as proteinuria, hematuria, hemolytic uremic syndrome and renal failure; dermatologic toxicity such as rash and alopecia; edema toxicities such as edema and peripheral edema; and, other toxicity such as fever. This anti-proliferative agent has been used to treat pancreatic and non-small cell lung cancers (*Compendium of Pharmaceutical and Specialties Thirty-fifth Edition,* 2000).

The present discussion comprises prevention or treatment of localized cancers or solid tumors that can be treated include those of the prostate, breast, pancreas, liver, kidney, genitourinary system, brain, gastrointestinal system, respiratory system, and head and neck. The compositions, etc., herein may prevent or treat cancers, including metastases, by allowing controlled release of high-sulfate fucan at a site somewhat distant from the target tumors by allowing effective concentrations of the high-sulfate fucan to reach the tumors and/or metastases by diffusion or even systemic transport. Some of these cancers are discussed further in the following paragraphs.

Prostate Cancer

Prostate cancer is a malignant tumor that arises in the cells lining the prostate gland. In the U.S., an estimated 200,000 patients will develop prostate cancer this year, and more than 30,000 will die of the disease. Prostate cancer has a death to new cases ratio of ~15%. The cancer may remain within the prostate, or it may spread to surrounding tissues or to distant sites (most often lymph nodes and bone). Usually prostate cancer spreads silently, producing symptoms only when it has progressed beyond the prostate. If prostate cancer has been diagnosed and treated during early stages, in some studies patients have had a 5-year survival rate of 94%.

Prostate cancer is often discussed as a disease of men over age 50. In fact, 80% of men with prostate cancer are 60 years of age and older. A man's chances of being diagnosed with prostate cancer during his lifetime are about 1 in 10, roughly the same as a woman's chances of having breast cancer. The number of reported new cases has risen dramatically in recent years as a result of improved tests that can detect the disease early in its development, often long before symptoms appear. The likelihood of developing prostate cancer in any given year increases with age but rises dramatically after age 50.

Current treatment options for prostate cancer depend upon the extent of disease progression, the patient's age and overall health. Elderly patients, who have only early stage cancer or who suffer from additional, more serious diseases, may be treated conservatively, whereas those whose cancer is advanced may undergo more aggressive treatment. Prostate cancer has been treated by various methods, including radiation therapy (external beam radiation or brachytherapy), hormone withdrawal or castration (surgical or chemical), anti-proliferative agents, surgery, and expectant therapy (that is, "watchful waiting"). No treatment guarantees an absolute cure, and some have considerable side effects.

Early stage prostate cancer (that is, the tumor is localized to the prostate) may be treated with "watchful waiting". Surgery for prostate cancer has been recommended for patients whose overall health has been otherwise good and the tumor is confined to the prostate gland. A common treatment for localized cancer of the prostate in men under the age of 70 has been radical prostatectomy (that is, surgical removal of the prostate).

Patients whose cancer is localized in the prostate area are commonly treated with external beam radiation (EBR). The radiation kills cancer cells and shrinks tumors. EBR accounts for less than 20% of localized prostate cancer treatment, with approximately 50% of these patients experiencing post radiation recurrences of the disease. Combined with early stage prostate cancer detection and increased demand from patients, brachytherapy (i.e., local radiation therapy) use has been expected to grow. In 1995, only 2.5% of newly diagnosed patients were treated using brachytherapy. Brachytherapy involves the implantation of radioactive metal "seeds" in the prostate tumor.

Treatment for prostate cancer that has spread involves removal of the testicles or hormone therapy. Both are used to inhibit or stop the production of the testosterone that has been driving the cancer growth. Approximately 20% of all prostate cancer patients undergo hormone withdrawal therapy. Hormone therapies include goserelin acetate (Zoladex®) or leuprolide acetate (Lupron®). Anti-proliferative agents used to treat prostate cancer have included 5-fluorouracil.

Breast Cancer

In the U.S., breast cancer has been the most common cancer among women, with about 180,000 new cases diagnosed every year (male breast cancer accounts for about 5% of all diagnosed breast cancers). It has been surpassed only by lung cancer as a cause of death in women, and it has been responsible for approximately 50,000 deaths annually. An American woman has a one in eight (or about 13%) chance of developing breast cancer during her lifetime. Over the past decade, most reported breast cancers were small, primary (arising independently; not caused by a metastasis) tumors. Roughly 70% to 80% of newly diagnosed patients exhibited early-stage disease (Stage 1 or 2), and a majority had no involvement of the axillary (underarm) lymph nodes.

Most breast cancers are carcinomas (that is, malignant tumors that grow out of epithelial tissues). Less than 1% of breast cancers are sarcomas, or tumors arising from connective tissue, bone, muscle or fat. In addition, most breast cancers (about 75%) are ductal carcinomas, arising in the tissues that line the milk ducts. A much smaller number of cancers (about 7%) are found within the breast lobules and are called lobular carcinomas. Paget's disease (cancer of the areola and nipple) and inflammatory carcinoma account for nearly all other forms of breast cancer.

Breast cancer treatment has been complicated and depends on many factors. Two important factors are the type of tumor and the stage of progression. Tumor characteristics, in particular, help to separate individuals into two groups: (1) those who are at low risk of cancer recurrence and (2) those who are at high risk of cancer recurrence. Specific prognostic factors place patients in either of these groups. These factors include tumor size; presence of female sex hormone estrogen and progesterone (ER/PR) receptors; cellular growth cycle phase (whether tumor cells are actively dividing or are in "S-phase"); presence of a protein known as "her-2-neu protein"; tumor grade, an indicator of tumor cell differentiation or change; and, tumor ploidy, the number of sets of genetic material within tumor cells.

Treatment of primary disease without significant lymph node involvement has been by lumpectomy and radiotherapy. More significant lymph node involvement may warrant mastectomy and removal of auxiliary lymph nodes. At this stage the chance of metastasis and local recurrence has been high. Treatment of metastatic disease has been palliative, involving radiation therapy and chemotherapy, which are immunosuppressive, cytotoxic and leukopenia. Anti-proliferative agents including, for example, 5-fluorouracil, doxorubicin, methotrexate, and paclitaxel, have been approved for use against breast cancer.

Pancreatic Cancer

The pancreas is an organ of the digestive system located near the stomach and small intestine. It has two major functions: the production of enzymes and hormones. Cancers of the pancreas can occur in the exocrine (i.e., enzymes) pancreas (e.g., classic pancreatic adenocarcinomas) or can occur in the endocrine (i.e., hormones) pancreas.

Cancers of the exocrine pancreas are a very serious health issue. In the U.S., approximately 28,000 patients are diagnosed with pancreatic cancer, while about the same number die annually from this disease. Pancreatic cancer occurs equally in males and females. Due to difficulties in diagnosis, the intrinsic aggressive nature of pancreatic cancers, and the sparse systemic treatment options available, only approximately 4% of patients diagnosed with pancreatic adenocarcinoma live for 5 years after diagnosis. Pancreatic cancer has been the 5' leading cause of cancer death, following breast, lung, colon, and prostate cancer.

The choice of treatment for pancreatic cancer depends largely on the stage of the tumor. Possible treatments include surgery, anti-proliferative agents, radiation, and biological therapy. Surgery has been usually reserved for Stage 1 patients whose cancer is deemed resectable. Sometimes a combination of therapies, such as radiation and anti-proliferative agent given before or after surgery, can increase a patient's chances of survival. Pancreatic cancer that is deemed unresectable (usually Stage II or later) may be treated using anti-proliferative agents in clinical trials. Anti-proliferative agents, such as, for example, gemcitabine or 5-fluorouracil have had some effect against pancreatic cancer and gemcitabine has been used as a palliative agent. Toxicities due to these anti-proliferative agents are discussed elsewhere herein. Radiation therapy has some effect against pancreatic cancer when used in combination with chemotherapy. Radiation therapy alone may subdue symptoms. This form of treatment has also been used in Stage II or later pancreatic cancers.

Bladder Cancer

In 1998, it was estimated that over 54,000 new cases of bladder cancer would be diagnosed in the U.S. and about 15,000 deaths would be attributed to the disease. Bladder cancer has been the fourth most common cancer among American men and the ninth most common cancer among American women. It occurs three times more frequently in men than in women. Primarily a disease of older men, bladder cancer has been a significant cause of illness and death. The risk of bladder cancer increases steeply with age (80% of cases occur in people older than 50 years), with over half of all bladder cancer deaths occurring after age 70. In white men over 65, the annual disease rate of bladder cancer has been approximately 2 cases per 1,000 persons; this contrasts with a rate of 0.1 cases per 1,000 persons under 65. During one's lifetime, the probability of developing bladder cancer has been greater than 3%; however, the probability of dying, from bladder cancer has been small (<1%). Bladder cancer rarely occurs in people who are younger than 40 years of age.

Recent studies suggest that certain genes and inherited metabolic abilities may play a role in bladder cancer. Transitional cell carcinoma (TCC) has been the most common form of bladder cancer. TCC usually occurs as a superficial (surface), papillary (wart-like), exophytic (outward-growing) mass upon a stalk-like base. In some cases, though, TCC may be attached on a broad base or it may appear ulcerated (within an indented lesion). Papillary TCCs often start out as areas of hyperplasia that later dedifferentiate or lose individual cell characteristics. Only about 10% to 30% of papillary TCCs develop into invasive cancers. By contrast, nonpapillary forms of TCC are more likely to become invasive. As noted, such TCCs may appear ulcerated or flat. Flat, nonpapillary TCC that has been made up of anaplastic epithelium has been classified as carcinoma in situ (CIS or TIS). The tissue of CIS contains cells that are large, have noticeable nucleoli (round body within a cell; involved in protein synthesis), and lack normal polarity.

The treatment of bladder cancer depends upon many factors. The most important of these factors are the type of tumor that is present and its stage. Common treatments include transurethral resection (TUR), electrosurgery, laser surgery, intravesical therapy, anti-proliferative agents, surgical therapy, cystectomy, and radiation therapy. Examples of anti-proliferative agents used to treat bladder cancer include, for example, 5-fluorouracil, cisplatin and methotrexate. Toxicities due to the anti-proliferative agents, 5-fluorouracil, cisplatin, and methotrexate, are discussed elsewhere herein.

Brain Cancer

Brain tumors are often inoperable and more than 80% of patients die within 12 months of diagnosis. Approximately 18,000 new cases of primary intracranial (brain) cancer are diagnosed each year in the U.S. This represents about 2 percent of all adult cancers. More than 50 percent of these are high-grade gliomas (i.e., glioblastoma multiform and anaplastic astrocytoma tumors). Patients with these tumors often suffer from severe disabilities such as motor dysfunction, seizures, and vision abnormalities.

Tumors that begin in brain tissue are known as primary brain tumors. Primary brain tumors are classified by the type of tissue in which they begin. The most common brain tumors are gliomas, which begin in the glial (supportive) tissue. Others include astrocytomas, brain stem gliomas, ependymomas and oligodendrogliomas.

Surgical removal of brain tumors has been recommended for most types and in most locations and should be as complete as possible within the constraints of preservation of neurologic function. An exception to this rule has been for deep-seated tumors, such as pontine gliomas, which are diagnosed on clinical evidence and are treated without initial surgery approximately 50% of the time. In many cases, however, diagnosis by biopsy is performed. Stereotaxic biopsy can be used for lesions that are difficult to reach and resect. Patients who have brain tumors that are either infrequently curable or unresectable should be considered candidates for clinical trials that evaluate radiosensitizers, hyperthermia, or interstitial brachytherapy used in conjunction with external-beam radiation therapy to improve local control of the tumor or for studies that evaluate new drugs and biological response modifiers.

Radiation therapy has a major role in the treatment of most tumor types and can increase the cure rate or prolong disease-free survival. Radiation therapy may also be useful in the treatment of recurrences in patients treated initially with surgery alone. Chemotherapy may be used before, during, or after surgery and radiation therapy. Recurrent tumors are treated with chemotherapy as well. Anti-proliferative agents used in the treatment of brain cancers include cisplatin. Examples of the toxicities associated with this anti-proliferative agent are discussed elsewhere herein.

Restenosis

Restenosis is a form of chronic vascular injury leading to vessel wall thickening and loss of blood flow to the tissue supplied by the blood vessel. This inflammatory disease can occur in response to vascular reconstructive procedures including any manipulation that relieves vessel obstruction. Thus, restenosis has been a major restrictive factor limiting the effectiveness of these procedures.

The present discussion comprises prevention or treatment of restenosis, for example by administering to a blood vessel a therapeutically effective amount of the combination of an oligonucleotide therapeutic and an anti-inflammatory agent. Suitable compositions include a polymeric carrier that can be surgically implanted at a restenosis site, or potential restenosis site, or can be injected via a catheter as a polymeric paste or gel. Suitable compositions may comprise high-sulfate fucans discussed herein.

Arthritis

Rheumatoid arthritis (RA) is a debilitating chronic inflammatory disease characterized by pain, swelling, synovial cell proliferation (pannus formation) and destruction of joint tissue. In the advanced stage, the disease often damages critical organs and may be fatal. The disease involves multiple members of the immune system (macrophages/monocytes, neutrophils, B cells and T cells) complex cytokine interactions and synovial cell malfunction and proliferation. Early aggressive treatment has been recommended with disease modifying anti-rheumatic drugs (DMARDs) such as methotrexate, which drug is discussed elsewhere herein.

Crystal induced arthritis has been characterized by crystal induced activation of macrophages and neutrophils in the joints and is followed by excruciating pain for many days. The disease progresses so that the intervals between episodes gets shorter and morbidity for the patient increases. This disease has been generally treated symptomatically with non-steroidal anti-inflammatory drugs (NSAIDs) such as diclofenac sodium (Voltaren®). This anti-inflammatory agent has toxicities which include central nervous system toxicities such as dizziness and headache; dermatologic toxicities such as rash and pruritus; gastrointestinal toxicities such as exacerbated ulcerative colitis and Crohn's disease; genitourinary toxicities such as acute renal failure and renal papillary necrosis; hematologic toxicities such as agranulocytosis, leukopenia and thrombocytopenia; hepatic toxicities such as elevated liver transaminases and hepatitis; and, other toxicities such as asthma and anaphylaxis.

The present discussion comprises prevention or treatment of rheumatoid arthritis, for example via administering to a patient a therapeutically effective amount of an oligonucleotide therapeutic and optionally an anti-inflammatory agent. Suitable compositions include a polymeric carrier that can be injected into a joint as a controlled release carrier of the anti-inflammatory agent and microparticulates as controlled release carriers of the oligonucleotide therapeutic (which in turn has been incorporated in the polymeric carrier). Suitable compositions may comprise high-sulfate fucans discussed herein. Such polymeric carriers may take the form of polymeric microspheres, pastes or gels.

Inflammatory Conditions

The compositions, etc., herein may optionally inhibit or treat inflammatory conditions involving neutrophils for example comprising administering to a patient compositions containing an oligonucleotide therapeutic and an anti-inflammatory agent. Examples of such conditions include crystal-induced arthritis; osteoarthritis; non-rheumatoid inflammatory arthritis; mixed connective tissue disease; Sjögren's syndrome; ankylosing spondylitis; Behçet's syndrome; sarcoidosis; psoriasis; eczema; inflammatory bowel disease; chronic inflammatory lung disease; neurological disorders; and, multiple sclerosis. Some of these diseases are discussed further in the following paragraphs.

Chronic Inflammatory Skin Diseases (Including Psoriasis and Eczema)

Psoriasis is a common, chronic inflammatory skin disease characterized by raised, thickened and scaly lesions which itch, burn, sting and bleed easily. While these diseases have cellular proliferation and angiogenic components in later stages of the disease, patients often have accompanying arthritic conditions. Symptoms may be treated with steroidal anti-inflammatory agents such as prednisone or anti-proliferative agents such as methotrexate, which agents are discussed elsewhere herein. The compositions herein may also be used to inhibit or otherwise treat and/or prevent chronic inflammatory skin diseases, for example psoriasis and/or eczema.

The following provides some additional representative examples of inflammatory diseases that can be treated with compositions discussed herein, include, for example, arterial embolization in arteriovenous malformations (vascular malformations); menorrhagia; acute bleeding; central nervous system disorders; and, hypersplenism; inflammatory skin diseases such as psoriasis; eczematous disease (atopic dermatitis, contact dermatitis, eczema); immunobullous disease; and, inflammatory arthritis which includes a variety of conditions including rheumatoid arthritis, mixed connective tissue disease, Sjögren's syndrome, ankylosing spondylitis, Behçet's syndrome, sarcoidosis, crystal induced arthritis and osteoarthritis (all of which feature inflamed, painful joints as a prominent symptom).

Ischemia

Ischemia or ischaemia involves a restriction in blood supply, which may include a shortage of supply of oxygen, glucose and other components required for proper tissue function, resulting in damage and/or dysfunction of tissue. Ischemia can cause severe problems. For example, tissues can become anoxic, necrotic, and clots can form. Various attempts have been made to prevent and/or treat ischemia. For example, restoration of blood flow, or reperfusion. Restoration of blood, however, involves the reintroduction of oxygen, which can cause additional damage due to the production of free radicals, resulting in reperfusion injury. Reperfusion injury can cause severe problems. The compositions herein may be used to inhibit or otherwise treat and/or prevent, ischemia, and/or reperfusion injury.

Endotoxemia

Endotoxemia is the presence of endotoxins in the blood. Endotoxemia can cause severe problems. For example, endotoxemia can lead to septic shock. The compositions herein may be used to inhibit, or otherwise treat and/or prevent, endotoxemia.

Keloid Scarring

Keloid trait causes wounds to heal with raised scars. Keloid traits' raised scars involve abnormal fibrous scarring. Keloid trait causes severe problems, for example pain and disfigurement. The compositions herein may be used to inhibit, or otherwise treat and/or prevent, keloid trait and its resulting raised scars.

Keloid (keloid scar) is a type of scar that expands in growths over normal skin. Keloids involve abnormal collagen growth, including type I and type III collage abnormal growth. Keloids cause severe problems, for example, pain, itchiness, and if infected may ulcerate. Attempts have been made to treat or prevent keloids including the use of surgery, dressings, steroid injections and laser therapy. The compositions herein may be used to inhibit, or otherwise treat and/or prevent, keloids.

Dermatitis

Dermatitis includes inflammation of the skin including atopic dermatitis and contact dermatitis. For example, contact dermatitis involves localized rash and/or irritation of the skin following contact of the skin with a foreign substance. For example, atopic dermatitis is a chronically relapsing, pruritic skin disease. Atopic dermatitis is sometimes called prurigo Besnier, neurodermitis, endogenous eczema, flexural eczema, infantile eczema, childhood eczema and prurigo diathsique. Eczema is a disease in a form of dermatitis. Other types of dermatitis include spongiotic dermatitis, seborrhoeic dermatitis (dandruff), dyshidrotic dermatitis (pompholyx), urticaria, vesicular dermatitis (bullous dermatitis), and popular urticaria. Dermatitis can cause severe problems. For example, dry skin, skin rashes, skin edema, skin redness, skin itchiness, skin crusting, cracking, blistering, oozing and bleeding. Attempts have been made to treat or prevent dermatitis including the use of corticosteroids and coal tars. The compositions herein may be used to inhibit, or otherwise treat and/or prevent, dermatitis including atopic dermatitis, eczema, contact dermatitis, spongiotic dermatitis, seborrhoeic dermatitis, dyshidrotic dermatitis, urticaria, vesicular dermatitis, and popular urticaria.

Rosacea

Rosacea is a chronic disease or condition typically characterized by facial erythema. Rosacea can cause severe problems. For example, rosacea typically begins as redness on the forehead, nose or cheeks and can also cause redness on the neck, ears, scalp and chest. For example, rosacea can cause additional symptoms including telangiectasia, papules, pustules, painful sensations, and in advanced cases rhinophyma (red lobulated nose) may develop. Rosacea subtypes include erythematotelangiectatic rosacea, papulopustular rosacea, phymatous rosacea, and ocular rosacea. Attempts have been made to treat or prevent rosacea including the use of anti-inflammatories and antibiotics. The compositions herein may be used to inhibit, or otherwise treat and/or prevent, rosacea including its erythematotelangiectatic, papulopustular, rosacea and ocular subtypes.

Medical Device, Medical Material, Combination, and Pharmaceutical Products

The discussion herein also provides medical devices, medical materials, combination, and pharmaceutical products, comprising compositions as discussed herein in a medical device, medical materials, combination product or pharmaceutically acceptable container. The products can also include a notice associated with the container, typically in a form prescribed by a governing agency regulating the manufacture, use, or sale of medical devices, medical materials, combination, and pharmaceuticals or biopharmaceuticals, whereby the notice is reflective of approval by the agency of the compositions, such as a notice that a high-sulfate fucan has been approved as an anti-proliferative agent or anti-inflammatory agent, e.g., for human or veterinary administration to treat proliferative diseases or inflammatory diseases (such as, for example, inflammatory arthritis, restenosis, surgical adhesions, psoriasis and peritonitis). Instructions for the use of the high-sulfate fucan herein may also be included. Such instructions may include information relating to the dosing of a patient and the mode of administration.

The present application is further directed to methods of making the various elements of the high-sulfate fucan, systems etc., discussed herein, including making the fucans and compositions themselves, as well as to methods of using the same, including for example treatment of the conditions, diseases, etc., herein.

The present application further comprises medical devices, medical materials, medical combination products, and pharmaceutical products for treatment of fibrous adhesions, arthritis, psoriasis or other diseases as desired comprising high-sulfate fucans and high-sulfate fucan compositions presented herein. The materials, etc., can be used in a medicament for treating fibrous adhesions, such as a surgical adhesions, arthritis, psoriasis or other diseases as desired. Also provided are methods of manufacturing and using such medicaments able to reduce symptoms associated with at least one of fibrous adhesions, arthritis, and psoriasis in a patient including a human patient, comprising combining a pharmaceutically effective amount of a fucan such as fucoidan as discussed herein with a pharmaceutically acceptable excipient or buffer.

The following Examples provide exemplary discussions of certain embodiments herein but the disclosure and claims are not limited thereto.

Example 1: Chemical Structural Modification

An exudate-extract was obtained from *Laminaria Hyperborea*. The exudate-extract was filtered and small molecules were removed by tangential flow filtration (TFF) over a 100 kDa filter. A sample of the resulting retentate was lyophilized to obtain otherwise unmodified sample A. The resulting retentate was brought to 0.25 M NaOH by addition of 10 M NaOH solution and left at room temperature for 16 hours. The resulting sample was then centrifugally filtered over a 50 kDa filter and the resulting retentate collected and lyophilized to obtain base-treated sample B. Both of unmodified sample A and base-treated sample B were analyzed by proton nuclear magnetic resonance spectroscopy ($^1$H-NMR) and the resulting $^1$H-NMR spectrum are shown in FIG. 1A.

FIG. 1A demonstrates the chemical structural modification of the fucan accomplished, the broad peak with a chemical shift about 2.0 ppm that is present in the unmodified sample A is not present in the base-treated sample B.

Unmodified sample A and base-treated/modified sample B were further analyzed by 2D $^1$H-$^{13}$C heteronuclear multiple quantum coherence (HMQC). The HMQC spectra, shown in FIG. 1B, were acquired at 70° C. with solvent signal suppression on a 600 MHz spectrometer equipped with 5-mm cold probe. A high number of scans of the HMQC spectra were acquired in the range from 10-30 ppm in the carbon dimension in 8 increments of 256-512 scans each; such scans were combined to create the spectra in FIG. 1B.

Figure 1B:
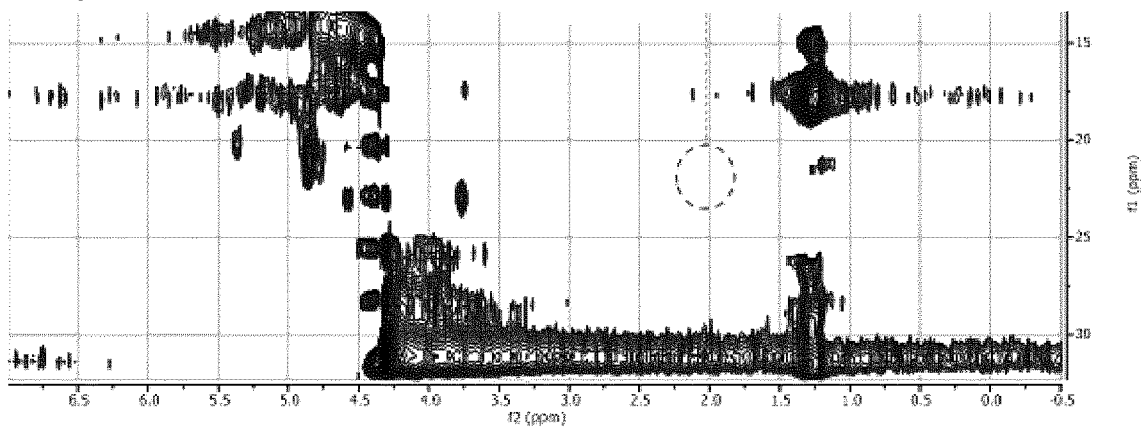
FIG. 1B depicts 2-D NMR results demonstrating that certain fucans treated according to methods herein undergo structural changes to the fucans.
Figure 1B:
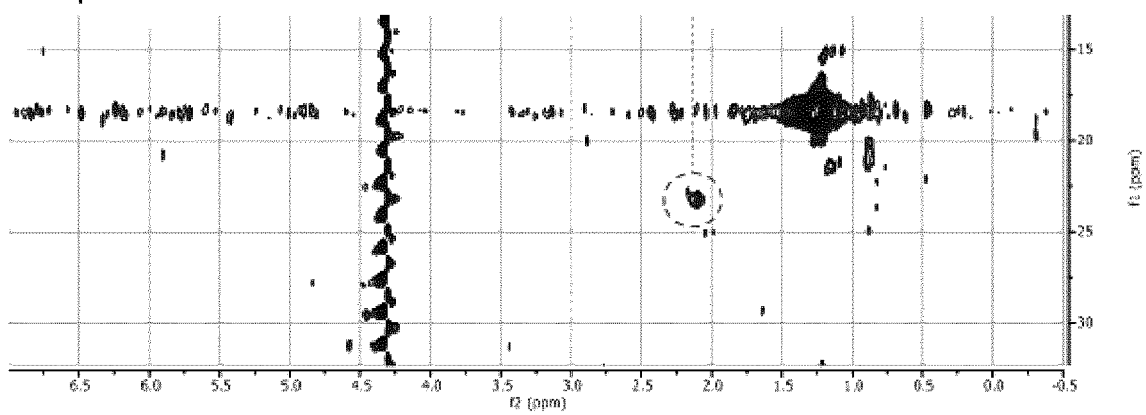

The HMQC spectra for unmodified sample A has a cross-peak corresponding to 0-acetyl groups, indicated by the signal circled in FIG. 1B. This cross-peak is not present in the spectra for base-treated sample B. This demonstrates the removal of acetyl groups from the fucan, and thus chemical structural modification of the fucan in base-treated sample B by the NaOH treatment.

Example 2: Chemical Desulfation

A feedstock fucoidan composition was dissolved in distilled water at 100 mg/mL to obtain a starting solution. The starting solution containing the feedstock fucoidan composition was brought to 60° C. on a hot plate. 10 M NaOH was added to the starting solution containing the feedstock fucoidan composition, obtaining a final NaOH concentration of 0.25 M NaOH and initiating the desulfation process. An aliquot was taken at 0.5 hours, 1 hour and every subsequent hour. Each aliquot was immediately neutralized with hydrochloric acid (HCl) to stop the desulfation process. The quenching of the base was confirmed by blotting about 0.1 mL of the quenched aliquot on pH paper.

Figure 2:
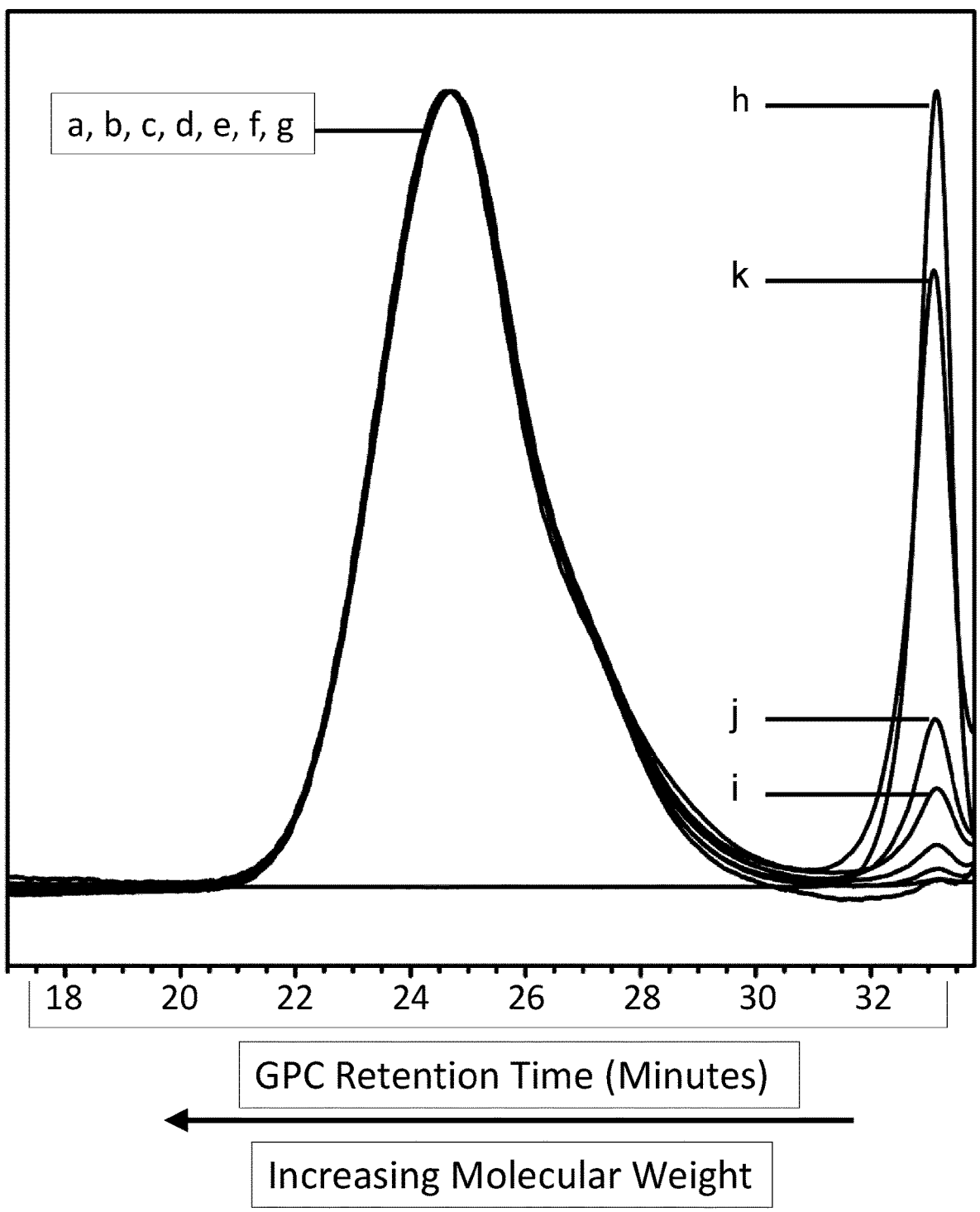
FIG. 2 provides a series of gel permeation chromatograms depicting different degrees of loss of sulfate from a starting fucan composition while leaving undegraded the resulting modified fucan.

Each aliquot was subjected to gel permeation chromatography (GPC) to monitor degradation and desulfation. A subset of the results obtained are shown in Table 1 in which some of the labels on the curves of FIG. 2 are identified. All gel permeation chromatography analyses for molecular weight determination were conducted using the following column configuration: 2× Ultrahydrogel® Linear in series with an Ultrahydrogel® guard. The mobile phase was 0.1M sodium nitrate run at 0.6 mL/min. The column and detector were held at 30° C. Detection was by means of a Waters 2414 refractive index detector.

Samples run were quantified against a standard curve comprising of traceable standards from the American Polymer Standards Corporation: DXT3755K (peak molecular weight=2164 kDa), DXT820K (peak molecular weight=745 kDa), DXT760K (peak molecular weight=621 kDa), DXT670K (peak molecular weight=401 kDa), DXT530K (peak molecular weight=490 kDa), DXT500K (peak molecular weight=390 kDa), DXT270K (peak molecular weight=196 kDa), DXT225K (peak molecular weight=213 kDa), DXT150K (peak molecular weight=124 kDa), DXT55K (peak molecular weight=50 kDa), DXT50K (peak molecular weight=44 kDa) and DXT5K (peak molecular weight=4 kDa), the peak molecular weights of these standards being between about 4 kDa and about 2,200 kDa. The standard curve used may, for example, include Dextran 3755 kDa, at least one of Dextran 50 kDa and Dextran 55 kDa, and between 3 to 6 additional traceable standards discussed herein, the calibration points being the peak molecular weights of the calibrants used. An example calibration curve may consist of DXT3755K, DXT 820K, DXT530K, DXT500K, DXT225K and DXT55K. The columns used herein had a total effective molecular weight range that encompassed and extended beyond the peak molecular weight range of the standards used for quantification of the fucans.

A sample of 10 mg/mL magnesium sulfate was dissolved in 0.1M sodium nitrate. Equilibration of some of the sulfate to the sodium form results in sodium sulfate. Desulfation of the feedstock fucoidan composition was qualitatively identified by the presence of a peak in the modified fucoidan chromatogram correlating to the sodium sulfate at about 33.1 minutes retention time. The presence of sodium sulfate is shown in Table 2 in which some of the labels on the curves of FIG. 2 are identified.

Results in the table below contain abbreviations used for certain characteristics of a molecular weight distribution. Gel permeation chromatography is denoted by GPC, peak retention time is denoted by PRT, peak molecular weight is denoted by PMW, weight average molecular weight is denoted by WAMW, number average molecular weight is denoted by NAMW, percentage distribution is denoted by % dist., molecular weight is denoted by MW, polydispersity index is denoted by PDI.

TABLE 1

Molecular weights of modified fucoidan using NaOH

|   |   | GPC PRT (Min) | PMW (kDa) | WAMW (kDa) | NAMW (kDa) | % dist. MW > 100 kDa | % dist. MW > 200 kDa | % dist. MW > 500 kDa | PDI | Sodium Sulfate peak? |
|---|---|---|---|---|---|---|---|---|---|---|
| a | Feedstock | 24.67 | 489.2 | 616.9 | 178.8 | 87.4 | 74.3 | 42.3 | 3.45 | No |
|   | Aliquot time (h) |   |   |   |   |   |   |   |   |   |
| b | 0.5 | 24.73 | 469.3 | 616.3 | 205.9 | 88.2 | 74.9 | 43.0 | 2.99 | No |
| c | 1 | 24.70 | 481.2 | 620.2 | 192.3 | 87.6 | 74.4 | 42.6 | 3.22 | Minor |
| d | 2 | 24.71 | 475.6 | 607.4 | 164.8 | 86.6 | 73.3 | 41.6 | 3.69 | Minor |
| e | 4 | 24.71 | 476.3 | 608.3 | 183.7 | 87.1 | 73.7 | 41.9 | 3.31 | Yes |
| f | 6 | 24.67 | 489.8 | 612.8 | 166.1 | 86.3 | 73.3 | 42.1 | 3.69 | Yes |
| g | 24 | 24.60 | 515.4 | 616.9 | 165.3 | 86.1 | 73.7 | 43.0 | 3.73 | Yes |

TABLE 2

Presence of sodium sulfate peak in modified fucoidans using NaOH

|   |   | GPC PRT (Min) |
|---|---|---|
| h | Sodium Sulfate Peak | 33.09 |
|   | Aliquot time (h) |   |
| i | 4 | 33.14 |
| j | 6 | 33.11 |
| k | 24 | 33.14 |

TABLE 3

Total sulfate in modified fucoidans using NaOH

|   | Concentration (mg/mL) | Total Sulfur (% w/w) | Total Sulfate (% w/w) |
|---|---|---|---|
| Feedstock | 3.75 | 14.7 | 44.2 |
| Aliquot time (h) |   |   |   |
| 1 | 3.75 | 14.2 | 42.7 |
| 4 | 2.70 | 14.0 | 42.1 |
| 24 | 3.00 | 13.5 | 40.4 |

Table 1, Table 2, and FIG. 2 show that the desulfation of a feedstock fucoidan composition has been achieved using a base such as sodium hydroxide. Treatment with sodium hydroxide results in controllable desulfation of a fucan composition without significantly degrading the fucoidan and without introducing unwanted additives in the desired modified fucan. The weight average molecular weight of the feedstock fucoidan composition does not change by more than 2% as a result of the methods discussed above, which is well within the error of the GPC instrumentation.

Example 3: Chemical Desulfation

A feedstock fucoidan composition was dissolved in 0.5 M NaOH at 50 mg/mL to obtain a starting solution. The starting solution containing the feedstock fucoidan composition was brought to 60° C. in a water bath, initiating the desulfation process. An aliquot was taken after 1 hour, 4 hours and 24 hours. Each aliquot was immediately neutralized with hydrochloric acid (HCl) to stop the desulfation process. The quenching of the base was confirmed by blotting about 0.1 mL of the quenched aliquot on pH paper.

Each neutralized aliquot was diafiltered against 6 volumes of 5 mM NaCl over a 10 kDa centrifugal filter. The resulting aliquot-retentates were diluted 3 parts in 20 parts distilled water. The concentration of the modified fucoidan in each diluted aliquot-retentate was determined by the total solids content and the results shown in Table 3 below. The diluted aliquot-retentates were analyzed by inductively coupled plasma-optical emission spectroscopy for total sulfur content, shown in Table 3 below. Sulfur content was converted to sulfate content by multiplying the sulfur content by the molar ratio of sulfate to sulfur to obtain % w/w sulfate content in the modified fucoidan.

Example 4: Chemical Sulfation

A starting fucan composition is dissolved at 10 mg/mL in distilled water to obtain about 500 mL of starting solution. The starting solution containing the starting fucan is protonated by recirculation over acidified Amberlite IR120 resin for about 30 minutes. The resulting acidified fucan composition in solution is lyophilized to obtain a solid acidified fucan composition. The solid acidified fucan composition is dissolved in a solvent mix of 40 mL formamide and 160 mL dimethylformamide containing about 15 g $SO_3$-DMF sulfation agent complex. 40 mL of 2-methyl-2-butene is added to the reaction mixture. The reaction mixture is incubated at 30° C. for 2 hours while stirring. After 2 hours, the reaction is quenched by addition of 200 mL of 5% w/v sodium bicarbonate. The resulting modified fucan is separated from the sulfation remnant molecules by tangential flow filtration over a 5 kDa TFF filter.

Example 5: Chemical Sulfation

About 5 g of a starting fucan composition is suspended in about 200 mL dichloromethane. About 1.6 mL of chlorosulfonic acid is added the suspension and the reaction mixture stirred at room temperature for 2 hours. The suspension is filtered through a paper filter and the resulting solid modified fucan is washed first with about 100 mL dichloromethane, then with about 100 mL of ethanol followed by 100 mL of dioxane. The washed solid modified fucan is dissolved in 5% w/v sodium bicarbonate solution and the resulting modified fucan is separated from the sulfation remnant molecules by tangential flow filtration over a 5 kDa TFF filter.

Production of Modified Fucans with Various Sulfation Ratios

Chemical sulfation, chemical desulfation or solvolytic desulfation methods may be used to control and/or modify the sulfation level of fucans in fucan compositions.

Example 6: Measurement of Fucose, Galactose and Sulfate Levels of Modified Fucans Eleven different fucan compositions were extracted from brown seaweed, the fucan compositions comprising essentially of fucans. The eleven modified fucans presented herein are referred to hereafter as fucan 1 to fucan 11. Fucan 1 to fucan 3, fucan 6 and fucan 8 were white solids. Fucan 4, fucan 5, fucan 7 and fucan 9 to fucan 11 were light brown solids. The modified fucans were dissolved in 72% w/w sulfuric acid at 40 mg/mL and incubated at 45° C. in a water bath for 30 minutes. The acid hydrolysate was then diluted to 4% w/w sulfuric acid in a high-pressure tube and incubated at 120° C. for 60 minutes. The resulting second acid hydrolysate is diluted to a 1/333 concentration with distilled water and run on high performance anionic exchange column chromatography set up with pulsed amperometry detection. Separation of analytes was accomplished over a Carbopac® PA20 analytical column by running 10 mM NaOH eluent at 1.0 mL/minute using an isocratic pump.

The fucose contents of the modified fucans were determined by interpolation on a standard curve for fucose. The galactose content of the modified fucans were determined by the method of standard addition.

The modified fucans were dissolved in deionized water, hydrolyzed under acidic conditions and analyzed by inductively coupled plasma mass spectrometry (ICP-MS) for % w/w total sulfur content, performed by ALS Environmental laboratories in Burnaby, British Columbia. Sulfur content was converted to sulfate content by multiplying the sulfur content by the molar ratio of sulfate to sulfur to obtain % w/w sulfate content in the modified fucan.

The % w/w results for total fucose, galactose and sulfate components are converted to molar ratios by dividing by the molar mass of the respective analyte. The molar ratio of total sulfate to total fucose, the molar ratio of total sulfate to total fucose plus galactose and the sulfation level for the eleven different modified fucans are shown in Table 4 below.

TABLE 4

Sulfation ratios of eleven fucans

| | Sulfate to Fucose Molar Ratio | Sulfate to Fucose + Galactose Molar Ratio | Sulfate (% w/w of fucan) |
|---|---|---|---|
| Fucan 1 | 2.05 | 1.85 | 44.9 |
| Fucan 2 | 2.41 | 1.42 | 39.8 |
| Fucan 3 | 2.18 | 1.36 | 40.4 |
| Fucan 4 | 1.20 | 1.18 | 22.7 |
| Fucan 5 | 0.57 | 0.49 | 11.4 |
| Fucan 6 | 1.94 | 1.75 | 41.3 |
| Fucan 7 | 0.89 | 0.65 | 12.3 |
| Fucan 8 | 1.93 | 1.79 | 51.3 |
| Fucan 9 | 2.82 | 1.35 | 23.9 |
| Fucan 10 | 1.97 | 1.66 | 14.4 |
| Fucan 11 | 1.72 | 1.54 | 25.6 |

Table 4 demonstrates modified fucans with various ratios of sulfation. The modified fucans have a molar ratio of total sulfate to total fucose of about 0.6 to about 2.9 and a molar ratio of total sulfate to total fucose plus galactose of about 0.5 to about 2.0.

Example 7: Measurement of Molecular Weight Distributions, Carbohydrate Content and Monosaccharide Components of Modified Fucans Modified fucans fucan 1, fucan 9, fucan 10 and fucan 11 were analyzed for total carbohydrate and monosaccharide composition by gas spectrometry-mass spectroscopy (GC-MS) performed by the complex carbohydrate research center at the University of Georgia. The modified fucan compositions were derivatized by acidic methanolysis to produce O-trimethylsilyl (O-TMS) derivatives. After derivatization, the modified fucan compositions were analyzed on an Agilent 7890A gas chromatography system interfaced to an Agilent 5975C mass spectrometry detector using a Supelco Equity-1 fused silica capillary column (30 m, 0.25 mm inner diameter). The results for the total carbohydrate content and the monosaccharide composition of the modified fucans are shown in table 5 below. Carbohydrate in the table below is abbreviated "carb.".

TABLE 5

Total carbohydrate and monosaccharide composition of four modified fucans

| | Total carb. content (% w/w of the fucan) | Fucose (% w/w of the total carb. content) | Galactose (% w/w of total carb. content) | Xylose (% w/w of total carb. content) | Mannose (% w/w of total carb. content) | Rhamnose (% w/w of total carb. content) |
|---|---|---|---|---|---|---|
| Fucan 1 | 59.50 | 91.85% | 8.11% | 0.00% | 0.00% | 0.00% |
| Fucan 9 | 32.70 | 44.43% | 52.93% | 0.50% | 0.41% | 0.33% |
| Fucan 10 | 25.90 | 48.26% | 9.88% | 15.48% | 5.89% | 0.29% |
| Fucan 11 | 30.10 | 84.72% | 10.63% | 3.32% | 0.89% | 0.00% |

Gel permeation chromatography was used to evaluate the molecular weight distributions obtained for the modified fucans fucan 1, fucan 2, fucan 3, fucan 6, fucan 8, fucan 9, fucan 10 and fucan 11. There are a large number of different parameters, columns and standards available for use in gel permeation chromatography, resulting in a variety of instrumentation set-ups available for the analysis of molecular weight. For molecular weight determinations herein, the GPC were conducted using the following parameters: The mobile phase was 0.1M sodium nitrate run at 0.6 mL/min. The column compartment and detector were at 30° C. A Waters 2414 refractive index detector was used for detection.

Suitable GPC columns include GPC columns compatible with aqueous solvents, for example, columns packed with at least one of sulfonated styrene-divinylbenzene, NH-functionalized acrylate copolymer network, modified silica and hydroxylated polymethacrylate-based gel. For the analyses herein, three columns were used in series, comprising one 40 mm long guard column with an inner diameter (ID) of 6 mm packed with 6 μm particle size hydroxylated polymethacrylate-based gel, followed by a first 300 mm analytical GPC column with a 7.8 mm ID packed with 12 μm particle size hydroxylated polymethacrylate-based gel that has an exclusion limit of about 7,000 kDa and an effective molecular weight range of between about 50 kDa and about 5,000 kDa, followed by a second 300 mm analytical GPC column with a 7.8 mm ID packed with 10 μm particle size hydroxylated polymethacrylate-based gel that has an exclusion limit of about 7,000 kDa and an effective molecular weight range of between about 1 kDa and about 6,000 kDa. The total effective molecular weight range of the column set up was between about 1 kDa and about 6,000 kDa. An example of this column set up can be Ultrahydrogel® guard-Ultrahydrogel® 2000-Ultrahydrogel® Linear columns connected in series.

Samples run were quantified against a standard curve comprising of traceable standards from the American Polymer Standards Corporation: DXT3755K (peak molecular weight=2164 kDa), DXT820K (peak molecular weight=745 kDa), DXT760K (peak molecular weight=621 kDa), DXT670K (peak molecular weight=401 kDa), DXT530K (peak molecular weight=490 kDa), DXT500K (peak molecular weight=390 kDa), DXT270K (peak molecular weight=196 kDa), DXT225K (peak molecular weight=213 kDa), DXT150K (peak molecular weight=124 kDa), DXT55K (peak molecular weight=50 kDa), DXT50K (peak molecular weight=44 kDa) and DXT5K (peak molecular weight=4 kDa), the peak molecular weights of these standards being between about 4 kDa and about 2,200 kDa. The standard curve used may, for example, include Dextran 3755 kDa, at least one of Dextran 50 kDa and Dextran 55 kDa, and between 3 to 6 additional traceable standards discussed herein, the calibration points being the peak molecular weights of the calibrants used. An example calibration curve may consist of DXT3755K, DXT 820K, DXT530K, DXT500K, DXT225K and DXT55K. The columns used herein had a total effective molecular weight range that encompassed and extended beyond the peak molecular weight range of the standards used for quantification of the fucans.

Results in table 6 below contain abbreviations used for certain characteristics of a molecular weight distribution. Gel permeation chromatography is denoted by GPC, peak molecular weight is denoted by PMW, weight average molecular weight is denoted by WAMW, number average molecular weight is denoted by NAMW, percentage distribution is denoted by % dist. and molecular weight is denoted by MW.

TABLE 6

Molecular weight distribution characteristics of four modified fucans

|  | PMW (kDa) | WAMW (kDa) | NAMW (kDa) | % dist. > 100 kDa | % dist. > 200 kDa | % dist. > 500 kDa |
|---|---|---|---|---|---|---|
| Fucan 1 | 457.33 | 592.80 | 300.92 | 95.393 | 82.93 | 43.837 |
| Fucan 2 | 409.39 | 772.00 | 291.78 | 93.96 | 81.49 | 43.61 |
| Fucan 3 | 393.10 | 930.12 | 296.59 | 93.60 | 81.08 | 43.60 |
| Fucan 6 | 515.76 | 693.27 | 311.07 | 94.91 | 83.50 | 49.38 |
| Fucan 8 | 686.21 | 1876.74 | 524.89 | 98.37 | 92.97 | 69.90 |
| Fucan 9 | 242.54 | 366.54 | 137.20 | 77.73 | 54.62 | 21.93 |
| Fucan 10 | 742.99 | 1617.97 | 387.52 | 92.90 | 86.60 | 68.20 |
| Fucan 11 | 6170.23 | 8101.88 | 846.27 | 94.67 | 91.11 | 83.56 |

Example 8: Epidural Fibrous Adhesion Treatment

Fucoidan solutions were prepared at 100 mg/mL from fucan 1 to fucan 4, fucan 7 and fucan 9 to fucan 11 in Lactated Ringers Injection USP (LRS). Fucoidan solution was prepared at 500 mg/mL from fucan 8 in Lactated Ringers Injection USP (LRS). Laminectomy surgery was performed on Sprague Dawley rats, the average weights of the rats and the dose in milligram per kilogram shown in table 7 below. A line block along the lumbar spine was created with bupivacaine solution. The back of the rat was cleaned and then covered with sterile drapes. The lumbar fascia was opened through a midline skin incision, lumbosacral fascia was incised and the paralumbar muscles were dissected to expose the underlying vertebral laminae. Bone at the center of the vertebrae was removed. Throughout the procedure, haemostasis was maintained by irrigation with Lactated Ringer's Injection USP (LRS) and pressure with cotton swabs. The exposed dura was treated directly with 15 microliters of either the LRS control or with fucoidan. The muscle and skin layers were closed with sutures and the rats were allowed to recover for one week before sacrifice for adhesion quantification. The presence and size of adhesions on the dura were noted. The dimensions of the adhesions and the exposed dura were recorded and used to calculate adhesion coverage percentage, being the adhesion area as a percentage of the total exposed dura area.

Adhesion coverage (%)=100×dura adhesion area $(mm^2)$÷total exposed dura area $(mm^2)$     Equation 1:

The control group receiving LRS was determined to have a 65% adhesion coverage using equation 1. The adhesion coverages for ten modified fucans disclosed in Table 4 are shown in Table 7 below as the reduction in adhesion coverage relative to the control group.

TABLE 7

Reduction in Rat Epidural Adhesion relative to control LRS using ten different fucans

| | Average Rat Weight (kg) | Dose (mg) | Dose per animal weight (mg/kg) | Number of Rats Scored | % Reduction in Rat Epidural Adhesion vs. Control |
|---|---|---|---|---|---|
| Fucan 1 | 0.58 | 1.5 | 2.6 | 2 | 100.0% (i.e., 100% reduction in fibrous adhesions compared to control) |
| Fucan 2 | 0.50 | 1.5 | 3.0 | 2 | 100.0% |
| Fucan 3 | 0.37 | 1.5 | 4.0 | 3 | 100.0% |
| Fucan 4 | 0.39 | 1.5 | 3.8 | 4 | −10.0% (i.e., 10% increase in fibrous adhesions compared to control) |
| Fucan 7 | 0.41 | 1.5 | 3.7 | 4 | −40.0% |
| Fucan 8 | 0.59 | 7.5 | 12.8 | 3 | 100.0% |
| Fucan 9 | 0.47 | 1.5 | 3.2 | 3 | 100.0% |
| Fucan 10 | 0.45 | 1.5 | 3.3 | 3 | 100.0% |
| Fucan 11 | 0.56 | 1.5 | 2.7 | 2 | 100.0% |

As may be seen from the result of Table 7, fucans comprising a molar ratio of total sulfate to total fucose greater than about 1.70 and a molar ratio of total sulfate to total fucose plus galactose greater than about 1.30 show a greater efficacy in the treatment of fibrous adhesions in comparison with fucans with a molar ratio of total sulfate to total fucose less than about 1.70 and a molar ratio of total sulfate to total fucose plus galactose less than about 1.30.

Example 9: Uterine Horn Fibrous Adhesion Treated with Fucan 6 and Fucan 7

The following double uterine horn (DUH) surgeries were performed on both horns of a total of two New Zealand White rabbits. Prior to surgery, the rabbits were weighed and then prepared for surgery by premedication with ketamine and xylazine.

Fucoidan solution was prepared at 0.07 mg/mL in Lactated Ringers Injection USP (LRS), sterilizing by filtration. All instruments were sterile, and a sterile field was maintained throughout the surgeries. The abdomen was cleaned and entered via a midline abdominal incision. The uterine horns were located, exteriorized and scraped to induce damage. The abdominal wall near the scraped uterine horns was also scraped. The damaged uterine horns and abdominal wall were placed next to each other and stabilized with sutures. 15 mL/kg fucoidan solution per rabbit weight was applied to the abdominal cavity before the incision was closed. Adhesion was evaluated two weeks after the surgery. Length of the uterine horn adhesion was measured with a ruler. The uterine horn adhesion coverage percentage, being the length of the adhesion as a percentage of the total damaged uterine horn length was calculated as:

Adhesion coverage (%)=100×uterine horn adhesion length÷total damaged uterine horn length    Equation 2:

The same surgical method was applied to three New Zealand White rabbits, receiving 15 mL/kg of Lactated Ringer's Injection USP (LRS) instead of fucoidan solution as a control group. The control group receiving LRS was determined to have a 41% adhesion coverage using equation 2. Table 8 shows the results obtained using the method described above for fucan 6 and fucan 7, being representative examples of a fucan with higher sulfation ratios and a fucan with lower sulfation ratios. The results in the table below are shown as the reduction in adhesion coverage relative to the control group.

TABLE 8

Reduction in rabbit uterine horn adhesion using fucan 6 and fucan 7

| | Dose (mg/kg) | Number of uterine horns scored | % Reduction in Rabbit DUH adhesion length |
|---|---|---|---|
| Fucan 6 | 1 | 8 | 100% |
| Fucan 7 | 1 | 6 | 21% |

As may be seen from the results of Table 8 fucans comprising a molar ratio of total sulfate to total fucose greater than about 1.90 and a molar ratio of total sulfate to total fucose plus galactose greater than about 1.70 show a greater efficacy in the treatment of fibrous adhesions in comparison to fucans with a molar ratio of total sulfate to total fucose less than about 1.90 and a molar ratio of total sulfate to total fucose plus galactose less than about 1.70.

Example 10: Uterine Horn Fibrous Adhesion Treated with Fucan 8

To determine the efficacy of the high-sulfate fucan 8 in inhibiting surgical adhesions, the following double uterine horn (DUH) surgeries were performed on both horns of a total of three New Zealand White rabbits. Prior to surgery, the rabbits were weighed and then prepared for surgery by premedication with ketamine and xylazine.

Fucoidan solution was prepared at 5 mg/mL in Lactated Ringers Injection USP (LRS), sterilizing by filtration. All instruments were sterile, and a sterile field was maintained throughout the surgeries. The abdomen was cleaned and entered via a midline abdominal incision. The uterine horns were located, exteriorized and scraped to induce damage. The abdominal wall near the scraped uterine horns was also scraped. The damaged uterine horns and abdominal wall were placed next to each other and stabilized with sutures. The top third and the bottom third of the muscle incision was closed and 5 mL/kg fucoidan solution per rabbit weight was applied to the abdominal cavity. The muscle incision was temporarily closed and the fucoidan solution left in the abdominal cavity for 30 minutes. The muscle incision was reopened and the abdominal cavity was flushed with 10 mL/kg LRS. The majority of the fluid in the abdominal cavity was suctioned out before the incision was closed. Adhesion formation was evaluated two weeks after the surgery. Length of the uterine horn adhesion was measured with a ruler. The uterine horn adhesion coverage percentage, being the length of the adhesion as a percentage of the total damaged uterine horn length was calculated using equation 2.

Table 9 shows the results obtained using the method discussed above for fucan 8, being a representative example of a high-sulfate fucan. The results in the table below are shown as the mean adhesion length across the 6 uterine horns scored.

Table 9 provides the results of treating six uterine horns with fucan 8.

TABLE 9

| | Adhesion length using fucan 8 | | |
|---|---|---|---|
| | Dose (mg/kg) | Number of Uterine Horns | Mean % adhesion length |
| Fucan 8 | 25 | 6 | 0% |

As may be seen from the results of Table 9, high-sulfate fucans may be used to successfully inhibit, prevent, remove, reduce, or otherwise treat post-surgical uterine horn adhesions.

Example 11: Uterine Horn Fibrous Adhesion Treated with Fucan 5

To determine the efficacy of the fucan 5 in inhibiting surgical adhesions, the following double uterine horn (DUH) surgeries were performed on both horns of a total of four New Zealand White rabbits. Prior to surgery, the rabbits were weighed and then prepared for surgery by premedication with ketamine and xylazine.

Fucoidan solution was prepared at 0.33 mg/mL in Lactated Ringers Injection USP (LRS), sterilizing by filtration. All instruments were sterile, and a sterile field was maintained throughout the surgeries. The abdomen was cleaned and entered via a midline abdominal incision. The uterine horns were located, exteriorized and scraped to induce damage. The abdominal wall near the scraped uterine horns was also scraped. The damaged uterine horns and abdominal wall were placed next to each other and stabilized with sutures. About 15 mL/kg fucoidan solution per rabbit weight was applied to the abdominal cavity before the incision was closed. Adhesion was evaluated two weeks after the surgery. Three rabbits were evaluated at each fucoidan concentration prepared. Length of the uterine horn adhesion was measured with a ruler. The uterine horn adhesion length was calculated using equation 2.

The same surgical method was applied to 4 New Zealand White rabbits, receiving about 15 mL/kg of control Lactated Ringer's Injection USP (LRS) instead of fucoidan solution. The control group receiving LRS was determined to have a 76% adhesion coverage using equation 2. Table 10 shows the results obtained using the method discussed above for fucan 5. The results in the table below are shown as the reduction in adhesion coverage relative to the control group.

Table 10 provides the result of treating eight uterine horns with fucan 5.

TABLE 10

| | Decrease in rabbit uterine horn adhesion using fucan 5 relative to control LRS. | | |
|---|---|---|---|
| | Dose (mg/kg) | Number of Uterine Horns | % Reduction in uterine horn adhesion coverage vs. control |
| Fucan 5 | 5 | 8 | 3.7% (i.e., 3.7% reduction in fibrous adhesions compared to control) |

As can be seen from the results of Table 10, fucan 5, being an example of a fucan with a total sulfate to total fucose ratio of below 1.3 and a total sulfate to total fucose plus galactose ratio of below 0.8, is not efficacious in the treatment of fibrous adhesions because there is no significant reduction in fibrous adhesions compared to the control group.

Example 12: Uterine Horn Fibrous Adhesion Treated with a High-Sulfate Fucan

To determine the efficacy of a high-sulfate fucan comprising a total sulfate of 45% w/w in inhibiting surgical adhesions, the following double uterine horn (DUH) surgeries were performed on both horns of a total of twenty New Zealand White rabbits. Prior to surgery, the rabbits were weighed and then prepared for surgery by premedication with midazolam and dexmeditomidine.

Fucoidan solution was prepared at each concentration of 0.02 mg/mL, 0.1 mg/mL, 0.5 mg/mL, or 2.5 mg/mL in Lactated Ringers Injection USP (LRS), sterilizing by filtration. All instruments were sterile, and a sterile field was maintained throughout the surgeries. The abdomen was cleaned and entered via a midline abdominal incision. The uterine horns were located, exteriorized and scraped to induce damage. The abdominal wall near the scraped uterine horns was also scraped. The damaged uterine horns and abdominal wall were placed next to each other and stabilized with sutures. About 2 mL/kg fucoidan solution per rabbit weight was applied to the abdominal cavity before the incision was closed. Adhesion was evaluated two weeks after the surgery. Five rabbits were treated and evaluated for each fucoidan concentration prepared. Length of the uterine horn adhesion was measured with a ruler. The uterine horn adhesion length was calculated using equation 2.

The same surgical method was applied to 5 additional New Zealand White rabbits for control, each receiving about 2 mL/kg of control Lactated Ringer's Injection USP (LRS) instead of fucoidan solution. The control group receiving LRS was determined to have a 100% adhesion coverage using equation 2. Table 11 shows the results obtained using the method discussed above for the high-sulfate fucan at different concentrations and dosages (in total forty uterine horns were treated, 10 each for each concentration of the high-sulfate fucan); the results are shown as the reduction in adhesion coverage relative to the control group.

TABLE 11

Decrease in rabbit uterine horn adhesion using
a high-sulfate fucan relative to control LRS

| Concentration (mg/mL) | Dose (mg/kg) | Number of Uterine Horns | % Reduction in uterine horn adhesion coverage vs. control |
|---|---|---|---|
| 0.02 | 0.04 | 10 | 10% (i.e., 10% decrease in fibrous adhesions compared to control) |
| 0.1 | 0.2 | 10 | 30% (i.e., 30% decrease in fibrous adhesions compared to control) |
| 0.5 | 1 | 10 | 71% (i.e., 71% decrease in fibrous adhesions compared to control) |
| 2.5 | 5 | 10 | 95% (i.e., 95% decrease in fibrous adhesions compared to control) |

As can be seen from the results of Table 11, high-sulfate fucan can be used to successfully inhibit, prevent, remove, reduce, or otherwise treat post-surgical uterine horn adhesions.

All terms used herein are used in accordance with their ordinary meanings unless the context or definition clearly indicates otherwise. Also unless expressly indicated otherwise, in this disclosure the use of "or" includes "and" and vice-versa. Non-limiting terms are not to be construed as limiting unless expressly stated, or the context clearly indicates, otherwise (for example, "including," "having," and "comprising" typically indicate "including without limitation"). Singular forms, including in the claims, such as "a," "an," and "the" include the plural reference unless expressly stated, or the context clearly indicates otherwise.

Unless otherwise stated, adjectives herein such as "substantially" and "about" that modify a condition or relationship characteristic of a feature or features of an embodiment, indicate that the condition or characteristic is defined to within tolerances that are acceptable for operation of the embodiment for an application for which it is intended.

The scope of the present methods, compositions, systems, etc., includes both means plus function and step plus function concepts. However, the claims are not to be interpreted as indicating a "means plus function" relationship unless the word "means" is specifically recited in a claim, and are to be interpreted as indicating a "means plus function" relationship where the word "means" is specifically recited in a claim. Similarly, the claims are not to be interpreted as indicating a "step plus function" relationship unless the word "step" is specifically recited in a claim, and are to be interpreted as indicating a "step plus function" relationship where the word "step" is specifically recited in a claim.

From the foregoing, it will be appreciated that, although specific embodiments have been discussed herein for purposes of illustration, various modifications may be made without deviating from the spirit and scope of the discussion herein. Accordingly, the systems and methods, etc., include such modifications as well as all permutations and combinations of the subject matter set forth herein and are not limited except as by the appended claims or other claim having adequate support in the discussion and figures herein.

What is claimed is:

1. A method of treating a fibrous adhesion in an animal comprising selecting a medically acceptable high-sulfate fucan composition to inhibit the fibrous adhesion and administering a therapeutically effective amount comprising a dosage range between 0.5 mg/kg and 50 mg/kg of the high-sulfate fucan to the site of a wound of the animal, wherein the medically acceptable high-sulfate fucan composition comprises a medically acceptable buffer or diluent and a therapeutically effective amount of a high-sulfate fucan having a sulfate to fucose molar ratio of between 1.2 and 1.9 and a sulfate to fucose plus galactose molar ratio of between 1.2 and 1.9.

2. A method of treating a fibrous adhesion at a target site in an animal, comprising selecting an agent for treating a fibrous adhesion and administering a therapeutically effective amount between about 0.04 mg/kg and 25 mg/kg of the high-sulfate fucan to the animal, and wherein the administering comprises administering the therapeutically effective amount to the target site, wherein the agent comprises a medically acceptable high-sulfate fucan composition comprising a medically acceptable buffer or diluent and a therapeutically effective amount of a high-sulfate fucan having a sulfate to fucose molar ratio of between 1.2 and 1.9 and a sulfate to fucose plus galactose molar ratio of between 1.2 and 1.9.

3. A method for treating fibrous adhesions in a patient comprising administering a medically acceptable high-sulfate fucan composition comprising a medically acceptable buffer or diluent and a therapeutically effective amount of a high-sulfate fucan having a sulfate to fucose molar ratio of between 1.2 and 1.9 and a sulfate to fucose plus galactose molar ratio of between 1.2 and 1.9.

4. A method for treating a fibrous adhesion in a patient comprising identifying a selected target site in a patient comprising or susceptible to having the fibrous adhesion and then administering an agent for treating the fibrous adhesion wherein the agent comprises a medically acceptable high-sulfate fucan composition comprising a medically acceptable buffer or diluent and a therapeutically effective amount of a high-sulfate fucan having a sulfate to fucose molar ratio of between 1.2 and 1.9 and a sulfate to fucose plus galactose molar ratio of between 1.2 and 1.9.

5. The method of claim 4 wherein the selected target site is a surgical site and the administering is performed at least one of a) after opening a surgical wound at the surgical site, b) during surgery, and c) after closing the surgical wound.

6. The method of claim 4 wherein the administering is performed after surgery but before closing the surgical wound.

7. The method of claim 4 wherein the administering takes less than 3 minutes.

8. The method of claim 4 wherein the administering takes less than 2 minutes.

9. The method of claim 4 wherein the administering takes less than 1 minute.

10. The method of claim 4 wherein the selected target site is at least one of a lesion, abrasion and injury site.

11. The method of claim 4 wherein the selected target site is at least one of a pelvic cavity, an abdominal cavity, a dorsal cavity, a cranial cavity, a spinal cavity, a ventral cavity, a thoracic cavity, a pleural cavity, a pericardial cavity, skin, a joint, a muscle, a tendon and a ligament.

12. The method of claim 1 wherein the high sulfate fucan composition comprises a high-sulfate fucan wherein a sulfate to fucose plus galactose molar ratio of the high-sulfate fucan is between 1.36 and 1.75.

13. The method of claim 1 wherein the high sulfate fucan composition comprises a high-sulfate fucan wherein the high-sulfate fucan has a molecular weight distribution wherein at least 60% w/w of the distribution is greater than 100 kDa when measured using an aqueous gel permeation chromatography set up consisting essentially of:

one 300 mm analytical gel permeation chromatography column with a 7.8 mm inner diameter packed with hydroxylated polymethacrylate-based gel, having an effective molecular weight range of between about 50 kDa and about 5,000 kDa, one 300 mm analytical gel permeation chromatography column with a 7.8 mm inner diameter packed with hydroxylated polymethacrylate-based gel, having an effective molecular weight range of between about 1 kDa and about 6,000 kDa and one 40 mm guard column with a 6 mm inner diameter packed with hydroxylated polymethacrylate-based gel, the two analytical gel permeation chromatography columns and the one guard column contained in a column compartment at about 30° C.;

a refractive index detector at about 30° C.;

0.1M sodium nitrate mobile phase run at 0.6 mL/min; and quantification against a peak molecular weight standard curve consisting essentially of a first dextran standard with a peak molecular weight of about 2,200 kDa, a second dextran standard with a peak molecular weight of between about 720 kDa and about 760 kDa, a third dextran standard with a peak molecular weight between about 470 kDa and about 510 kDa, a fourth dextran standard with a peak molecular weight between about 370 kDa and about 410 kDa, a fifth dextran standard with a peak molecular weight between about 180 kDa and about 220 kDa, and a sixth dextran standard with a peak molecular weight between about 40 kDa and 55 kDa.

14. The method of claim 1 wherein the high sulfate fucan composition comprises a high-sulfate fucan wherein the high-sulfate fucan has a sulfation level of between 14% w/w and 60% w/w.

15. The method of claim 1 wherein the high sulfate fucan composition comprises a high-sulfate fucan wherein the high-sulfate fucan has a total carbohydrate content between 27% w/w and 80% w/w.

16. The method of claim 1 wherein the medically acceptable high-sulfate fucan composition has a viscosity of between about 4 cP and 50 cP when dissolved in water at a concentration of 50 mg/mL.

17. A method for treating a fibrous adhesion in a patient comprising identifying a selected target site in a patient comprising or susceptible to having the fibrous adhesion and then administering the medical composition to the selected target site in the patient, wherein the medical composition is a medically acceptable high-sulfate fucan composition comprising a medically acceptable buffer or diluent and a therapeutically effective amount of a high-sulfate fucan having a sulfate to fucose molar ratio of between 1.2 and 1.9 and a sulfate to fucose plus galactose molar ratio of between 1.2 and 1.9.

* * * * *